(12) United States Patent
McManus et al.

(10) Patent No.: US 8,604,159 B2
(45) Date of Patent: Dec. 10, 2013

(54) METHOD FOR PREPARING FUNCTIONALIZED POLYMERS FROM POLYMER ALCOHOLS

(75) Inventors: Samuel P. McManus, Huntsville, AL (US); Antoni Kozlowski, Huntsville, AL (US); J. Milton Harris, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 850 days.

(21) Appl. No.: 10/897,386

(22) Filed: Jul. 22, 2004

(65) Prior Publication Data

US 2005/0054816 A1    Mar. 10, 2005

Related U.S. Application Data

(60) Provisional application No. 60/489,583, filed on Jul. 22, 2003.

(51) Int. Cl.
| | | |
|---|---|---|
| C08G 65/34 | (2006.01) | |
| A61K 31/74 | (2006.01) | |
| A61K 47/48 | (2006.01) | |
| C08G 63/48 | (2006.01) | |
| C08G 63/91 | (2006.01) | |
| C08L 89/00 | (2006.01) | |

(52) U.S. Cl.
USPC ............... 528/425; 424/78.17; 525/54.1

(58) Field of Classification Search
USPC ............... 528/425; 424/78.17; 525/54.1
See application file for complete search history.

(56) References Cited

U.S. PATENT DOCUMENTS

| | | | |
|---|---|---|---|
| 4,670,417 A | | 6/1987 | Iwasaki et al. |
| 5,252,710 A * | | 10/1993 | Dazey et al. ............... 530/383 |
| 5,252,714 A | | 10/1993 | Harris et al. |
| 5,281,698 A | | 1/1994 | Netecki |
| 5,468,478 A | | 11/1995 | Saifer et al. |
| 5,629,384 A | | 5/1997 | Veronese et al. |
| 5,650,234 A | | 7/1997 | Dolence et al. |
| 5,672,662 A | | 9/1997 | Harris et al. |
| 5,824,784 A | | 10/1998 | Kinstler et al. |
| 5,900,461 A | | 5/1999 | Harris |
| 5,932,462 A | | 8/1999 | Harris et al. |
| 6,362,254 B2 | | 3/2002 | Harris et al. |
| 6,376,604 B2 | | 4/2002 | Kozlowski |
| 6,448,369 B1 * | | 9/2002 | Bentley et al. ............... 528/425 |
| 6,455,639 B1 | | 9/2002 | Yasukohchi et al. |
| 6,602,498 B2 | | 8/2003 | Shen |
| 6,624,246 B2 | | 9/2003 | Kozlowski |
| 6,815,530 B2 | | 11/2004 | Ekwuribe et al. |
| 6,835,802 B2 | | 12/2004 | Ekwuribe et al. |
| 2002/0061557 A1 * | | 5/2002 | Nikolics et al. ............. 435/69.1 |
| 2003/0083389 A1 * | | 5/2003 | Kao et al. ..................... 516/98 |
| 2005/0036978 A1 * | | 2/2005 | Kozlowski ................. 424/78.17 |

FOREIGN PATENT DOCUMENTS

| | | |
|---|---|---|
| EP | 0 614 666 | 9/1994 |
| EP | 1 283 233 | 2/2003 |
| JP | 08165343 | 6/1996 |
| WO | 03/047549 | 6/2003 |
| WO | 2004/060965 | 7/2004 |
| WO | 2004/060966 | 7/2004 |

OTHER PUBLICATIONS

Goodson et al., "Site-Directed Pegylation of Recombinant Interleukin-2 at its Glycosylation Site", Biotechnology, Apr. 1990, vol. 8, pp. 343-346.

Kogan, "The Synthesis of Substituted Methoxy-Poly(Ethyleneglycol) Derivatives Suitable for Selective Protein Modification", Synthetic Communications (1992), vol. 22 No. 16, pp. 2417-2424.

Ouchi et al., "Design of Antitumor Agent-Terminated Poly(Ethylene Glycol) Conjugate as Macromolecular Prodrug", Polymer Preprints (1997), 38(1):582-583.

Romani et al., "Synthesis of Unsymmetrical Cystine Peptides: Directed Disulfide Pairing with the Sulfenohydrazide Method", Chem. Peptides and Proteins (1984), vol. 2, pp. 29-34.

Zalipsky and Barany, "Facile Synthesis of α-Hydroxy-ω-Carboxymethylpolyethylene Oxide", J. of Bioactive and Compatible Polymers, Apr. 1990, vol. 5 No. 2, pp. 227-231.

Harris, Milton J., "Laboratory Synthesis of Polyethylene Glycol Derivatives", JMS-Rev. Macromol. Chem. Phys., (1985), C25(3):325-373.

* cited by examiner

*Primary Examiner* — Nathan M Nutter
(74) *Attorney, Agent, or Firm* — Mark A. Wilson

(57) ABSTRACT

The present invention provides, among other things, methods for preparing functionalized and other polymers from polymer from polymer alcohols such as poly(ethylene glycol)s. In addition, polymer compositions, conjugates, polymeric reagents, are also provided.

46 Claims, 3 Drawing Sheets

METHOD FOR PREPARING FUNCTIONALIZED POLYMERS FROM POLYMER ALCOHOLS

CROSS REFERENCE TO RELATED APPLICATIONS

This application claims the benefit of priority to provisional application Ser. No. 60/489,583, Jul. 22, 2003, which is incorporated herein by reference.

FIELD OF THE INVENTION

Among other things, this invention relates to functionalized, water-soluble and non-peptidic polymers, and in particular, to methods for making, purifying, and utilizing such polymers.

Covalent attachment of the hydrophilic polymer, poly(ethylene glycol), abbreviated "PEG," to molecules and surfaces is of considerable utility in areas such as biotechnology and medicine. PEG is a polymer that possesses many beneficial properties. For instance, PEG is soluble in water and in many organic solvents, is non-toxic and non-immunogenic, and when attached to a surface, PEG provides a biocompatible, protective coating. Common applications or uses of PEG include (i) covalent attachment to proteins, e.g., for extending plasma half-life and reducing clearance through the kidney, (ii) covalent attachment to small molecules for improving water solubility and ease of formulation, and to reduce the rate of kidney clearance, (iii) attachment to surfaces such as in arterial replacements, blood contacting devices, and biosensors, (iv) as a soluble carrier for biopolymer synthesis, and (v) as a reagent in the preparation of hydrogels.

In many if not all of the uses noted above, it is necessary to first activate the PEG by converting its hydroxyl terminus to a functional group capable of readily reacting with a functional group found within a desired target molecule or surface, such as a functional group found on the surface of a protein. For proteins, typical reactive amino acids include lysine, cysteine, histidine, arginine, aspartic acid, glutamic acid, serine, threonine, tyrosine, the N-terminal amino group and the C-terminal carboxylic acid.

The PEG used as a starting material for most PEG activation reactions is typically an end-capped PEG. An end-capped PEG is one where one or more of the hydroxyl groups, typically located at a terminus of the polymer, is converted into a non-reactive group, such as a methoxy, ethoxy, or benzyloxy group. Most commonly used is methoxy PEG, abbreviated as mPEG. End-capped PEGs such as mPEG are generally preferred, since such end-capped PEGs are typically more resistant to cross-linking and aggregation. The structures of two commonly employed end-capped PEG alcohols, mPEG and monobenzyl PEG (otherwise known as bPEG), are shown below,

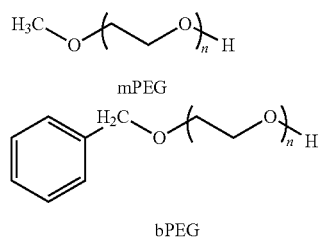

mPEG bPEG wherein n typically ranges from about 10 to about 2,000.

Although the use of mPEG is preferred in many respects, there are also some serious disadvantages associated with the use of mPEG as a starting material. Commercially available mPEG is often contaminated with PEG diol (HO—$(CH_2CH_2)_n$—OH), where values of n are typically as stated above. Although some manufacturers produce low-diol mPEG, some of the diol impurity is always present, and content can range as high as 10-15%, or in some cases, even greater. PEG diol arises from the presence of trace amounts of water contamination during the base catalyzed polymerization of ethylene oxide to form mPEG. Due to a lower concentration of methoxide initiator in the preparation of high molecular weight PEGs, e.g., exceeding 20 kilodaltons (K) or so, water contamination and hence diol formation can present a more serious problem. For high molecular weight PEG, diol contamination can reach or even exceed 30%. Further, because the diol chain can grow at each end, the contaminating diol typically has a higher average molecular weight than the desired mPEG.

One characteristic of PEGylation chemistry is that, in most cases, the diol and corresponding difunctional or di-activated PEG resulting from PEG diol are not removed. In such cases, the conjugate product will contain a certain amount of cross-linked product, and additionally possess an increased polydispersity due to polymer diol and diol-derived contaminants. This is highly undesirable for a pharmaceutical product, since the presence and amounts of such contaminants can be highly variable, thus leading to irreproducibility of the product.

Different approaches have been employed to date in an attempt to overcome these problems. In one approach to reduce the amount of diol impurity in mPEG starting materials, monofunctional PEG alcohols have been manufactured by polymerization of ethylene oxide under strictly anhydrous conditions using an alcohol initiator in the form of a sodium or potassium salt (Odian, Principles of Polymerization, $3^{rd}$ edition, Wiley, 1991; F. E. Bailey, Jr. & J. V. Koleske, in Poly(ethylene oxide), Academic Press, New York, 1976). Although resulting in mPEGs having somewhat reduced diol content, this approach does not lend itself to commercial scale syntheses, due to the sensitivity of the process to moisture and associated problems in controlling the molecular weight and polydispersity of the product. Moreover, the process is rather complicated and expensive to operate, especially for the manufacture of the relatively small quantities of higher molecular weight polymeric reagents needed for many pharmaceutical applications. Further, the explosive reactivity of the monomer requires additional safety precautions that add to the cost of manufacturing.

In another approach to dealing with diol contamination, crude benzyloxy PEG containing diol impurity is methylated and then hydrogenated to remove the benzyl group (See U.S. Pat. No. 6,448,369). As a result, PEG diol present in the composition is converted to the inert dimethyl ether. However, this process can be disadvantageous in several respects. First, this approach adds to the total number of synthetic steps that must be carried out to prepare a final activated PEG reagent or product. Secondly, although inert, this approach still leads to the formation of an impurity in the activated PEG composition.

Alternatively, an activated PEG product may be purified to remove difunctional material, however, such purifications are typically extremely laborious and time-consuming, as well as difficult to accomplish. For example, gradient-based chromatography, a frequently employed separations approach, requires the analysis of multiple eluate fractions, utilizes a large volume of solvent, and is poorly suited for commercial scale processes. Moreover, gradient-based separation techniques rarely achieve acceptable purity levels, particularly when separating higher molecular weight polymer species.

In sum, the present methods for preparing activated PEGs, particularly monofunctional activated PEGs, are unsatisfactory in many respects. For the most part, the current methods rely on the use of relatively expensive mPEG starting material, which often contains large amounts of the undesirable contaminant, PEG diol. Current synthetic approaches to avoid diol formation are complicated, requiring multiple additional reaction steps, and can still result in the formation of detectable amounts of PEG diol or PEG-diol derived byproducts. Finally, existing separations approaches, particular chromatographic methods, are unsatisfactory for the reasons discussed above.

The Applicants have realized a continuing need in the art for new methods for preparing activated PEGs that (i) do not rely on expensive monofunctional polymer starting materials, (ii) do not require multiple additional cumbersome reaction steps, and (iii) overcome the problems associated with the presence of PEG diol by providing high purity polymer reagents having a low diol content. In response to these and other needs, the Applicants have, among other things, developed new methods for forming activating PEGs which overcome many of the shortcomings noted above.

SUMMARY OF THE INVENTION

In one aspect, the invention provides a method for forming a functionalized polymer, the method comprising the steps of: (a) providing a water-soluble and non-peptidic polymer comprising two hydroxyl groups (i.e., a water-soluble and non-peptidic polymer having two or more hydroxyl groups); (b) reacting the water-soluble and non-peptidic polymer comprising two hydroxyl groups, in one or more reaction steps, with one or more functionalizing reagents to effect the introduction of a functional group, Y, to form a mixture comprising (i) unsubstituted water soluble and non-peptidic polymer from step (a), (ii) a monosubstituted polymer comprising a single Y group, and (iii) a disubstituted polymer comprising two Y groups, under conditions effective to form either no more than about 45 percent of the disubstituted polymer; and (c) purifying the mixture from step (b) to provide a monosubstituted polymer substantially free from the unsubstituted and disubstituted polymer species. Functionalized polymers, as well as monosubstituted polymers, prepared in accordance with this method represent additional aspects of the invention. The method optionally comprises the further step of alkylating the non-peptidic polymer comprising two hydroxyl groups prior to step (b), or alkylating the mixture formed in step (b) prior to or subsequent to the purification step (c). This optionally step can be used to convert unreacted hydroxyl groups to alkoxy groups.

In another aspect, the invention provides a method for forming an alkylated functionalized polymer, said method comprising the steps of: (a) providing a water-soluble and non-peptidic polymer comprising two hydroxyl groups; (b) alkylating the water-soluble and non-peptidic polymer to form a mixture comprising (i) unalkylated water-soluble and non-peptidic polymer from step (a), (ii) a monoalkylated polymer comprising a single alkoxy group, and (iii) a dialkylated polymer comprising two alkoxy groups, under conditions effective to form at least about 25 mol percent of the dialkylated polymer; (c) reacting the mixture from step (b), in one or more reaction steps, with one or more functionalizing reagents to effect the introduction of a functional group, Y, to form a mixture comprising (i) unalkylated polymer comprising two Y groups, a monoalkylated polymer comprising a single Y group, and a dialkylated polymer comprising no Y groups, (d) purifying the mixture from step (c) to provide a monoalkylated polymer substantially free from the unalkylated and dialkylated polymer species. Alkylated functionalized polymers, as well as monoalkylated polymers substantially free from the unalkylated and dialkylated polymers species, prepared in accordance with this method represent additional aspects of the invention.

In still another aspect, the invention provides a method of forming a functionalized polymer, the method comprising the steps of: (a) providing a polymer comprising a formula HO-POLY-OH, wherein POLY is a water-soluble and non-peptidic polymer; (b) optionally, converting HO-POLY-OH to a mixture comprising HO-POLY-OH, HO-POLY-Z and Z-POLY-Z, wherein Z is a leaving group, under conditions effective to form no more than about 45 percent of Z-POLY-Z; (c) reacting HO-POLY-OH of step (a) or the mixture of step (b) with a functionalizing reagent comprising the structure X-$L_{0,1}$-Y, wherein X is a group that reacts with a hydroxyl, optionally in anionic form, or with a carbon atom to which the hydroxyl or leaving group is attached, $L_{0,1}$ is an optional linker, and Y is an ionizable group, to form a mixture comprising HO-POLY-OH, HO-POLY-$L_{0,1}$-Y, and Y-$L_{0,1}$-POLY-$L_{0,1}$-Y, under conditions effective to form preferably no more than about 25 percent of Y-$L_{0,1}$-POLY-$L_{0,1}$-Y; (d) optionally, alkylating the mixture from step (b) or step (c); and (e) purifying the mixture from step (c) or step (d) by ion exchange chromatography to provide substantially pure polymer comprising a single -$L_{0,1}$-Y group. Functionalized polymers, as well as substantially pure polymer comprising a single -$L_{0,1}$-Y group, prepared in accordance with this method represent additional aspects of the invention.

In yet an additional aspect, the invention provides a method of separating a mixture of polymer species by ion exchange chromatography, said method comprising the steps of: (a) providing a mixture of water-soluble and non-peptidic polymers, said mixture comprising a neutral polymer absent an ionizable functional group, a monofunctional polymer comprising a single ionizable functional group, and a difunctional polymer comprising two ionizable functional groups; (b) passing the mixture through a first ion exchange column to provide an eluate, wherein said passing the mixture step is carried out under conditions effective to adsorb substantially all of the difunctional polymer onto the first column; (c) passing the eluate through a second ion exchange column under conditions effective to adsorb substantially all of the monofunctional polymer onto said second column; (e) washing the second column with water or a salt solution having low ionic strength to remove substantially only neutral polymer absent an ionizable functional group in a wash solution; and (f) passing a solution having sufficient ionic strength through the second column to desorb the monofunctional polymer.

In still another aspect, the invention provides an ion exchange chromatography apparatus, comprising: a supply of solution of a water-soluble and non-peptidic polymer mixture comprising a neutral polymer absent ionizable functional groups, a monofunctional polymer comprising a single ionizable functional group, and a difunctional polymer comprising two ionizable functional groups; a first ion exchange column comprising a first inlet, a first outlet, and a first ion exchange media, said first inlet being in fluid communication with said supply; a second ion exchange column comprising a second inlet, a second outlet, and a second ion exchange media, said second inlet being in fluid communication with said first outlet; and at least one product recovery vessel in fluid communication with said second outlet, adapted to receive eluent exiting from said second ion exchange column. The first and second ion exchange media can either be the same or different, and the apparatus includes instances where the first and second ion exchange media are the same and instances where the first and second ion exchange media are different.

BRIEF DESCRIPTION OF THE DRAWINGS

Figure 1:
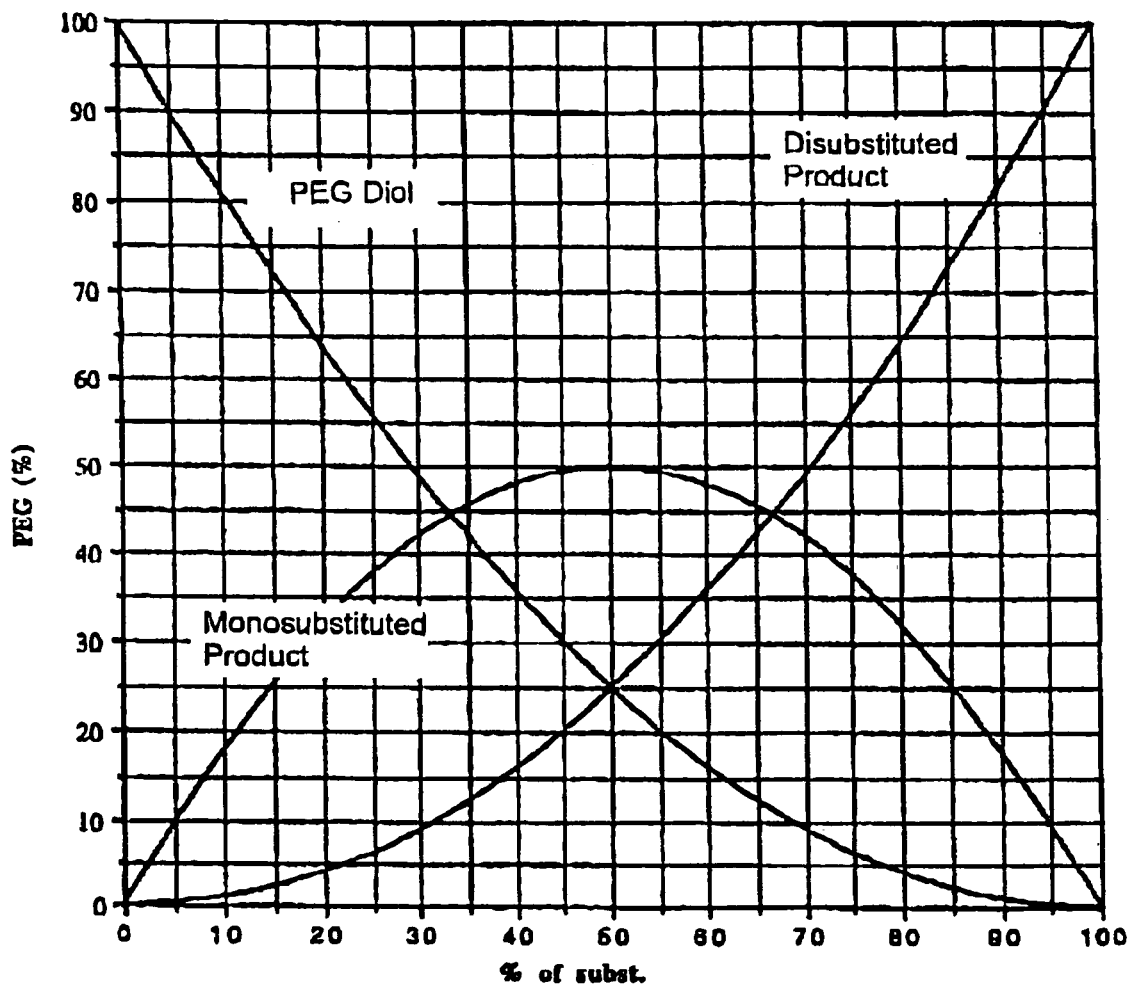
Figure 2:
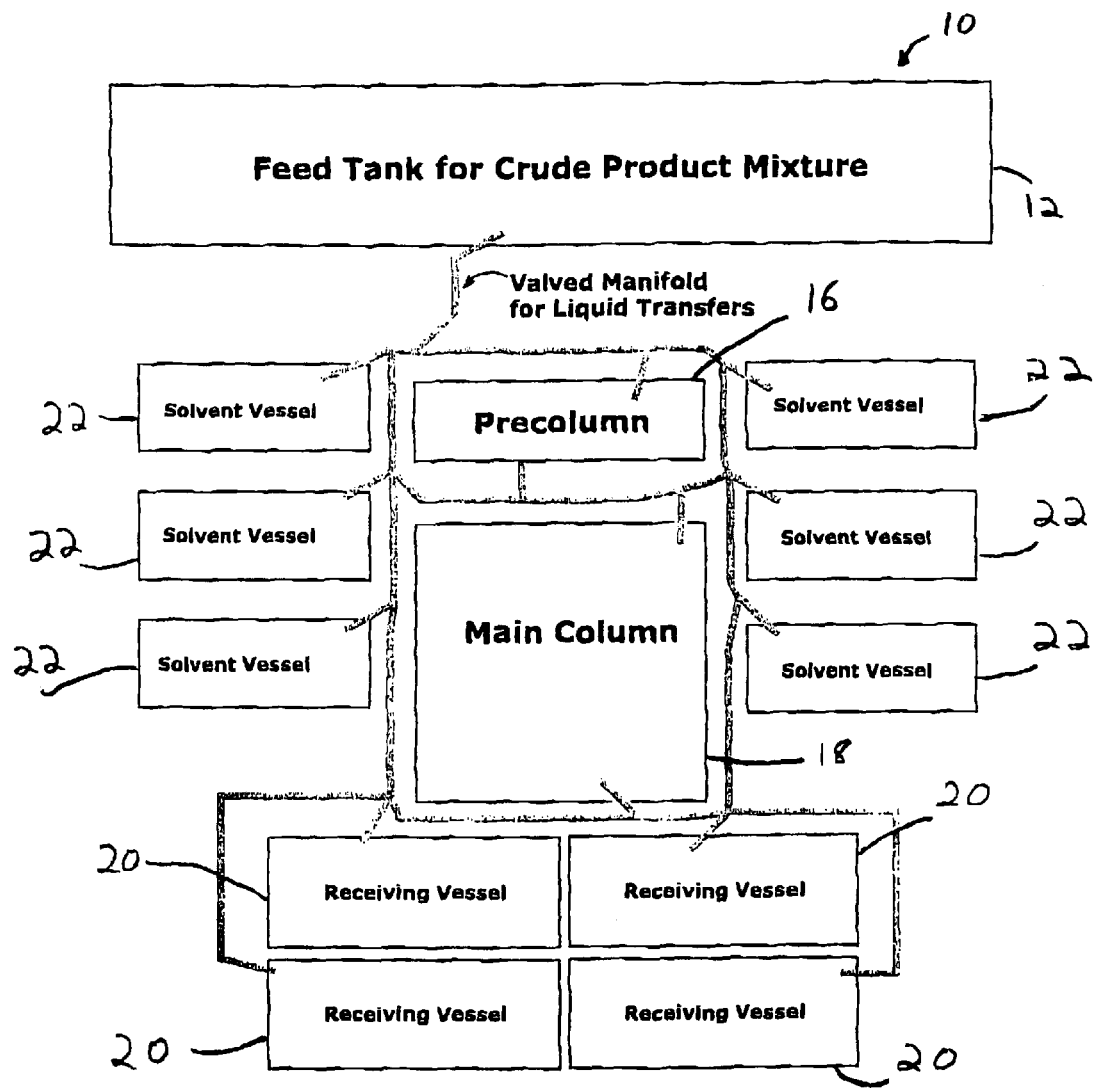
Figure 3:
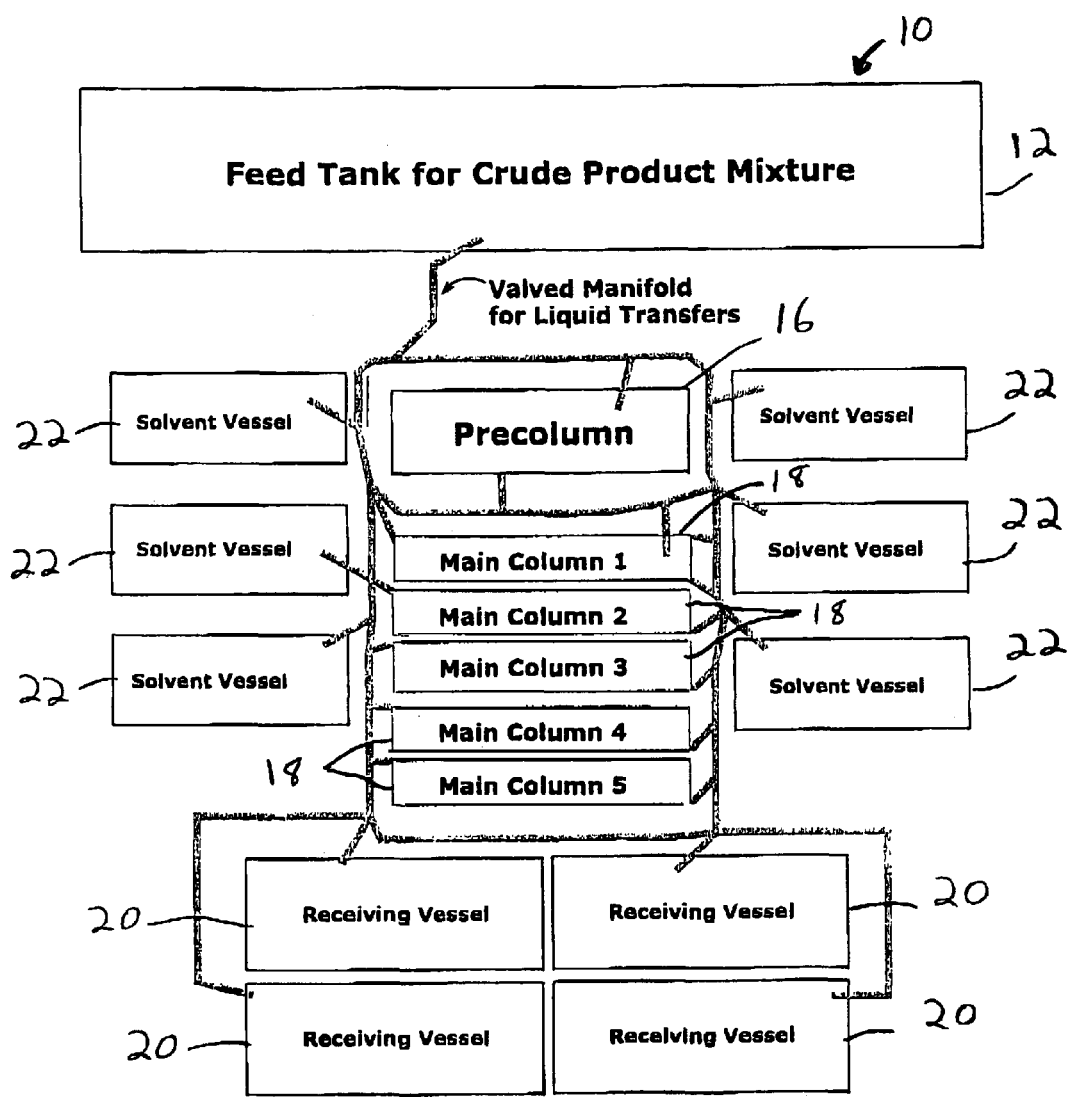

Having thus described the invention in general terms, reference will now be made to the accompanying drawings, wherein:

FIG. 1 graphically illustrates the statistics of substitution of a PEG diol in a nucleophilic substitution reaction. This plot demonstrates the relative concentrations of diol, mono- and di-substituted product in a reaction mixture at any point during such a reaction;

FIG. 2 illustrates an embodiment of the ion exchange chromatography system of the invention in which two columns are employed;

FIG. 3 illustrates a multiple column embodiment of the ion exchange chromatography system of the invention;

DETAILED DESCRIPTION OF THE INVENTION

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

I. DEFINITIONS

In describing and claiming the present invention, the following terminology will be used in accordance with the definitions described below.

"PEG," "polyethylene glycol" and "poly(ethylene glycol)" are used herein to mean any water-soluble poly(ethylene oxide). Typically, PEGs for use in the present invention will comprise one of the two following structures: "—O(CH$_2$CH$_2$O)$_n$—" or "—CH$_2$CH$_2$O(CH2CH$_2$O)$_n$—CH$_2$CH$_2$—," where n is 3 to 3000, and the terminal groups and architecture of the overall PEG may vary. "PEG" means a polymer that contains a majority, that is to say, greater than 50%, of subunits that are —CH$_2$CH$_2$O—.

One commonly employed PEG is end-capped PEG. When PEG is defined as "—O(CH$_2$CH$_2$O)$_n$—," the end-capping group is generally a carbon-containing group typically comprised of 1-20 carbons and is preferably alkyl (e.g., methyl, ethyl or benzyl) although saturated and unsaturated forms thereof, as well as aryl, heteroaryl, cyclo, heterocyclo, and substituted forms of any of the foregoing are also envisioned. When PEG is defined as "—CH$_2$CH$_2$O(CH$_2$CH$_2$O)$_n$—CH$_2$CH$_2$—," the end-capping group is generally a carbon-containing group typically comprised of 1-20 carbon atoms and an oxygen atom that is covalently bonded to the group and is available for covalently bonding to one terminus of the PEG. In this case, the group is typically, alkoxy (e.g., methoxy, ethoxy or benzyloxy) and with respect to the carbon-containing group can optionally be saturated and unsaturated, as well as aryl, heteroaryl, cyclo, heterocyclo, and substituted forms of any of the foregoing. The other ("non-end-capped") terminus is a typically hydroxyl, amine or an activated group that can be subjected to further chemical modification when PEG is defined as "—CH$_2$CH$_2$O(CH$_2$CH$_2$O)$_n$—CH$_2$CH$_2$—." In addition, the end-capping group can also be a silane.

Specific PEG forms for use in the invention include PEGs having a variety of molecular weights, structures or geometries (e.g., branched, linear, forked PEGs, multifunctional, and the like), to be described in greater detail below.

The end-capping group can also advantageously comprise a detectable label. When the polymer has an end-capping group comprising a detectable label, the amount or location of the polymer and/or the moiety (e.g., active agent) to which the polymer is coupled to is of interest can be determined by using a suitable detector. Such labels include, without limitation, fluorescers, chemiluminescers, moieties used in enzyme labeling, calorimetric (e.g., dyes), metal ions, radioactive moieties, and the like.

The polymers of the invention are typically polydisperse (i.e., number average molecular weight and weight average molecular weight of the polymers are not equal), possessing low polydispersity values—expressed as a ratio of weight average molecular weight (Mw) to number average molecular weight (Mn), (Mw/Mn)—of generally less than about 1.2, preferably less than about 1.15, more preferably less than about 1.10, still more preferably less than about 1.05, yet still most preferably less than about 1.03, and most preferably less than about 1.025.

As used herein, the term "ionizable functional group" and variations thereof is a functional group that may gain or lose a proton by interaction with another ionizable species of functional group in aqueous or other polar media. Ionizable functional groups include, but are not limited to, amine, carboxylic acids, aldehyde hydrates, ketone hydrates, amides, hydrazines, thiols, phenols, oximes, dithiopyridines, and vinylpyridines.

As used herein, the term "carboxylic acid" is a moiety having a

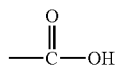

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. Reference is again made to Greene et al., "PROTECTIVE GROUPS IN ORGANIC SYNTESIS" 3$^{rd}$ Edition, John Wiley and Sons, Inc., New York, 1999.

"Activated carboxylic acid" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

The term "reactive" or "activated", when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link interconnecting moieties such as a terminus of a water-soluble polymer portion and a functional group. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, iso-butyl, tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like.

"Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyloxy, etc.), preferably $C_1$-$C_8$.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Electrophile" refers to an ion or atom or collection of atoms, that may be ionic, having an electrophilic center, i.e., a center that is electron seeking or capable of reacting with a nucleophile.

"Nucleophile" refers to an ion or atom or collection of atoms, that may be ionic, having a nucleophilic center, i.e., a center that is seeking an electrophilic center or capable of reacting with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multifunctional" or "multisubstituted" in the context of a polymer of the invention means a polymer having 2 or more functional groups contained therein, where the functional groups may be the same or different. Multifunctional polymers of the invention will typically contain from about 2-100 functional groups, or from 2-50 functional groups, or from 2-25 functional groups, or from 2-15 functional groups, or from 3 to 10 functional groups, or will contain 2, 3, 4, 5, 6, 7, 8, 9 or 10 functional groups within the polymer backbone.

A "difunctional" or "disubstituted" polymer means a polymer having two functional groups contained therein, either the same (i.e., homodifunctional) or different (i.e., heterodifunctional).

A "monofunctional" or "monosubstituted" polymer means a polymer having a single functional group contained therein (e.g., an mPEG based polymer).

A basic or acidic reactant described herein includes neutral, charged, and any corresponding salt forms thereof.

The term "patient," refers to a living organism suffering from or prone to a condition that can be prevented or treated by administration of a conjugate, and includes both humans and animals.

"Optional" or "optionally" means that the subsequently described circumstance may or may not occur, so that the description includes instances where the circumstance occurs and instances where it does not.

Unless otherwise noted, molecular weight is expressed herein as number average molecular weight ($M_n$), which is defined as $$\frac{\sum N_i M_i}{\sum N_i},$$

wherein $N_i$ is the number of polymer molecules (or the number of moles of those molecules) having molecular weight $M_i$.

Each of the terms "drug," "biologically active molecule," "biologically active moiety," "active agent" and "biologically active agent", when used herein, means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

The term "conjugate" is intended to refer to the entity formed as a result of covalent attachment of a molecule, e.g., a biologically active molecule, to a reactive polymer molecule, preferably poly(ethylene glycol).

"Eluate" refers to a solution that has passed through a chromatography column (i.e., an effluent stream).

"Eluent" refers to the mobile phase utilized during a chromatographic separation.

"Pre-column" and "first column" are used interchangeably herein and refer to a single chromatography column, as well as two or more columns connected in series that serve as the "pre-column" or "first column." In addition, the terms "main column" and "second column" are used interchangeably herein and refer to a single chromatography column, as well as two or more columns connected in series that serve as the "main column" or "second column."

II. METHOD OF PREPARING FUNCTIONALIZED POLYMERS USING POLYMERIC POLYOL STARTING MATERIAL

In one aspect, the present invention provides a method of forming functionalized polymeric reagents, particularly monofunctional polymeric reagents, using polymeric polyol starting materials, such as dihydroxy PEG, instead of the expensive, difficult to purify mPEG starting materials known in the art. The method of the invention involves reacting the polymeric polyol starting material with a functionalizing reagent comprising a functional group, —Y. The functionalizing reagent is capable of reaction, in one or more steps, with the polyol to form a plurality of substituted polymers, each comprising a varying number of —Y groups. The reaction is typically carried out under conditions effective to produce a mixture of an unsubstituted polymer (i.e., the original polymeric polyol), a monosubstituted polymer (i.e., a polymer having a single Y group), and one or more multisubstituted polymers (e.g., a disubstituted polymer having two Y groups) characterized by a relatively wide difference in content of the monosubstituted product and the multisubstituted product(s).

The mixture of polymer products is subjected to a purification step in order to separate the mixture components and provide a monosubstituted polymer substantially free from the unsubstituted and multisubstituted polymer species. By performing the purification/separation process while the desired monosubstituted polymer and the multisubstituted polymer species are present at differing concentrations, separation is made easier and formation of highly pure monofunctional polymeric reagents is possible. In essence, controlling the extent to which the functionalizing reaction is allowed to proceed is used as a means to enhance and simplify separation of the polymeric species formed in the reaction. The approach of the present invention is particularly well suited for use with functionalizing reagents that attach ionizable functional groups to the polymer and separation processes adapted for separation based on differences in charge.

For purposes of illustrating one or more advantages of the invention, the use of a dihydroxy PEG staring material is considered. Commencement of a reaction of the dihydroxy PEG with a functionalizing reagent comprising a protected amine or protected carboxylic acid will result in formation of a monosubstituted polymer species (e.g., a polymer having a single protected or free amine or protected or free carboxylic acid group) and a disubstituted polymer species (e.g., a polymer having two protected amine or protected carboxylic acid groups). As the number of moles of the mono- and disubstituted polymers increases, the number of moles of the original PEG diol starting material will decrease concomitantly. The theoretical yield of monosubstituted and disubstituted polymer species expressed as a % of substitution (i.e., mole percent) is shown in FIG. 1. As shown, the monosubstituted product reaches a theoretical maximum of 50% and then declines as the percentage of disubstituted product continually increases. The amount of unsubstituted PEG diol starting material continually declines as the reaction proceeds.

In one or more embodiments of the present invention, the reaction is allowed to proceed until a certain predetermined amount of the monosubstituted and disubstituted polymer species is formed. This predetermined amount is selected based on the disparity in concentration of the monosubstituted product and the disubstituted product. By stopping the reaction at a point characterized by a large difference in concentration of the monosubstituted product and the disubstituted product (e.g., when the reaction mixture comprises 25.5% monosubstituted product and only 2.25% disubstituted product), separation or purification of the polymer mixture is easier. As noted above, this is particularly true when ionizable groups are utilized that allow separation of the polymer mixture based on differences in charge.

Once the functionalizing reaction ends (e.g., by quenching or reagent exhaustion) at the desired point, separation of the mixture can take place and the purified monosubstituted polymer can then be used, optionally after further functionalization, for any one of a number of purposes (e.g., to form a conjugate with a biologically active agent). Further functionalization can be carried out by subjecting the purified monosubstituted polymer to additional reaction steps to form other useful active polymeric reagents, such as the formation of active esters from carboxylic acid terminated polymers or the formation of maleimides from amine terminated polymers.

Examples of suitable functional groups that can be formed on the final purified polymer include hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, and p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, glyoxal, dione, mesylate, tosylate, and tresylate. Exemplary functional groups are discussed in the following references: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

If a monofunctional end-capped polymer is desired, the method of the invention can also include an alkylation step, which can occur either before or after the polymer polyol staring material is reacted with the functionalizing agent. Preferably, the optional alkylation step occurs after the functionalizing reaction so that the functionalizing step remains the controlling step in the process that determines the relative concentrations of the monosubstituted polymer product as compared to the disubstituted or other multisubstituted polymer species. If the alkylating step is performed before the reaction with the functionalizing reagent, then the alkylating step becomes the controlling reaction that determines the desired disparity in monosubstituted polymer content versus disubstituted polymer content. Alternatively, the alkylation step can be avoided by utilizing a polymeric mixture of a polymeric diol and its monoalkylated form (e.g., mPEG) if such mixtures having a proper balance of the two components are readily available.

As discussed in greater detail below, the functional group, Y, is preferably an ionizable functional group. Exemplary ionizable functional groups include amine and carboxylic acid groups. Examples of other suitable functional groups include aldehyde hydrate, ketone hydrate, amide, hydrazine, hydrazide, thiol, phenol, oxime, other alkanoic acids having a carbon length (including the carbonyl carbon) of 1 to about 25 carbon atoms (e.g., carboxymethyl, propanoic acid, and butanoic acid), dithiopyridine, and vinylpyridine.

A. Polyol Starting Materials

A polymeric polyol can be used in the present invention and can comprise any water soluble and non-peptidic polymer having at least two hydroxyl groups covalently attached thereto. Preferably, the polymeric polyol is a diol (i.e., a polymer having two hydroxyl groups attached thereto); however, polyols containing greater than 2 hydroxyl groups can be utilized, such as polyols comprising about 3-100 hydroxyl groups, or from 3-50 hydroxyl groups, or from 3-25 hydroxyl groups, or from 3-15 hydroxyl groups, or from 3 to 10 hydroxyl groups, or will contain 3, 4, 5, 6, 7, 8, 9 or 10 hydroxyl groups attached to the polymer. Although the hydroxyl groups are preferably attached to the termini of the polymer, the hydroxyl groups may also be attached to the polymer as side chains in pendant fashion.

The polymer should be non-toxic and biocompatible, meaning that the polymer is capable of coexistence with living tissues or organisms without causing harm. When referring to the polymeric polyol, it is to be understood that the polymer can be any of a number of water soluble and non-peptidic polymers, such as those described herein as suitable for use in the present invention. Preferably, poly (ethylene glycol) (i.e., PEG) is the polymeric polyol. The term PEG includes poly(ethylene glycol) in any of a number of geometries or forms, including linear forms, branched or multi-arm forms (e.g., forked PEG or PEG attached to a polyol core), pendant PEG, or PEG with degradable linkages therein, to be more fully described below.

Multi-armed or branched PEG molecules, such as those described in U.S. Pat. No. 5,932,462, which is incorporated by reference herein in its entirety, can also be used as the PEG polymer. Generally speaking, a multi-armed or branched polymer possesses two or more polymer "arms" extending from a central branch point (e.g., C in Formula II below). For example, an exemplary branched PEG polymer has the structure:

Formula I wherein $PEG_1$ and $PEG_2$ are PEG polymers in any of the forms or geometries described herein, and which can be the same or different, and L' is a hydrolytically stable linkage. An exemplary branched PEG of Formula I has the structure:

Formula II wherein: $poly_a$ and $poly_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine.

The branched PEG structure of Formula II can be attached to a third oligomer or polymer chain as shown below:

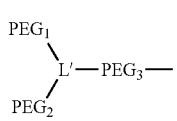

Formula III wherein $PEG_3$ is a third PEG oligomer or polymer chain, which can be the same or different from $PEG_1$ and $PEG_2$.

The PEG polymer may alternatively comprise a forked PEG. Generally speaking, a polymer having a forked structure is characterized as having a polymer chain attached to two or more functional groups via covalent linkages extending from a hydrolytically stable branch point in the polymer. An example of a forked PEG is represented by PEG-L-CHY$_2$, where L is a linking group and Y is a functional group. Each Y group is linked to CH by a chain of atoms of defined length. U.S. Pat. No. 6,362,254, the contents of which are incorporated by reference herein, discloses various forked PEG structures capable of use in the present invention. The chain of atoms linking the Y functional groups to the branching carbon atom serve as a tethering group and may comprise, for example, an alkyl chain, ether linkage, ester linkage, amide linkage, or combinations thereof.

As noted above, the PEG polymer may comprise a pendant PEG molecule having reactive groups, such as hydroxyl, covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more hydrolytically stable or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

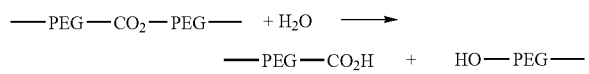

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; and oligonucleotide linkages formed by, for example, a phosphoramidite group, e.g., at the end of a polymer, and a 5' hydroxyl group of an oligonucleotide.

It is understood by those skilled in the art that the term poly(ethylene glycol) or PEG represents or includes all the above forms of PEG.

Any of a variety of other polymeric polyols comprising other non-peptidic and water soluble polymer chains can also be used in the present invention. The polymeric polyol can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof.

Different polymers can be incorporated into the same polymer backbone. For example, one or more of the PEG molecules in the branched structures shown in Formulas I-III can be replaced with a different polymer type. Any combination of water soluble and non-peptidic polymers is encompassed within the present invention.

The molecular weight of the polymeric polyol will vary depending on the desired application, the configuration of the polymer structure, the degree of branching, and the like. Generally, polymers having a molecular weight of about 100 Da to about 180,000 Da are useful in the present invention, preferably about 500 Da to about 60,000 Da, and more preferably about 5,000 Da to about 40,000 Da. Exemplary polymer embodiments have a molecular weight of approximately 1,000 Da, 2,000 Da, 3,000 Da, 4,000 Da, 5,000 Da, 7,500 Da, 10,000 Da, 15,000 Da, 20,000 Da, 25,000 Da, 30,000 Da, 35,000 Da, and 40,000 Da.

The polymeric polyol is typically dissolved in water or an organic solvent prior to the functionalizing reaction discussed below. Any organic solvent compatible with polymers of the type used in the present invention can be utilized, such as toluene, xylene, benzene, dichloromethane, chloroform, acetonitrile, tetrahydrofuran, or acetone. Mixtures of the above solvents or other similar solvents known in the art also can be used.

B. Functionalizing Reaction

The reaction step or steps used to react a functionalizing reagent with the polymeric polyol can vary depending on a number of factors, including the type of functional group involved, the type and configuration of the polymer, and so forth. The exact nature of the reaction sequence is not critical to the present invention and any known method of functionalizing polymers of the type used in the present invention can be utilized without departing from the invention.

As noted above, in one embodiment, the functionalizing reaction is only allowed to proceed under conditions effective to produce a product mixture characterized by a wide difference in the concentrations of the monosubstituted product and the di- or other multisubstituted products. Preferably, the reaction is also conducted under conditions effective to produce a relatively low content of multisubstituted product. To achieve the desired content disparity, the reaction between the polyol starting material and the functionalizing reagent can be stopped or quenched at the appropriate time using any method known in the art, such as by rapidly changing process parameters (e.g., temperature or degree of mixing) or by carefully controlling the amount of reactants, thereby controlling the reaction on a stoichiometric basis. The appropriate time for stopping or quenching the reaction can be determined by obtaining periodic samples of the reaction mixture and determining the amount of species present (e.g., by chromatographic methods, NMR methods and so forth) or by measuring a parameter (e.g., pH) known to correlate with the amount of species present. Alternatively, if a significant deficiency of the functionalizing reagent is charged, the reaction will only proceed to partial conversion of the diol. In this instance, the reaction may be allowed to proceed to completion. In such cases, knowing the stoichiometry of the reactants allows for the estimation of the final compositional components when reference is made to FIG. 1.

The reaction is generally performed under conditions effective to form no more than about 45 percent of the disubstituted polymer. Reactions allowed to continue past this point result in disubstituted polymer being present in an amount greater than monosubstituted polymer, with the result that separation becomes increasingly inefficient. While no more than about 45 percent of the disubstituted polymer is typically allowed to form, it is often preferred that the percent of disubstituted polymer formation is encompassed in one or more of the following ranges: no more than about 40 percent; no more than about 35 percent; no more than about 30 percent; no more than about 25 percent; no more than about 20 percent; no more than about 15 percent; no more than about 12 percent, and nor more than about 10 percent. In certain embodiments, no more than about 8 percent, preferably no more than about 5 percent, more preferably no more than about 2 percent, and most preferably no more than about 1 percent of the disubstituted polymer is formed. In certain embodiments, the functionalizing reaction results in a ratio of monosubstituted polymer to disubstituted polymer from about 2:1 to about 40:1, preferably about 4:1 to about 20:1, and more preferably about 10:1 to about 18:1.

Typically, the final functionalized polymer mixture will comprise about 8 percent to about 50 percent of the monosubstituted polymer, preferably about 8 to about 45 percent, and more preferably about 8 to about 30 percent. The final functionalized polymer mixture will typically comprise about 1 to about 45 percent of the disubstituted polymer, preferably about 1 to about 12 percent, and more preferably about 1 to about 5 percent. Generally, the final functionalized polymer mixture will comprise about 10 to about 91 percent of the original unsubstituted polymeric polyol, preferably about 43 to about 91 percent, more preferably about 65 to about 91 percent.

The functionalizing reaction typically comprises a nucleophilic substitution reaction or a nucleophilic addition reaction (e.g., a Michael addition reaction), wherein the nucleophile can be present on the polymer or the functionalizing reagent. For example, the reaction can involve reaction of a hydroxyl group of the polymeric polyol, or an anion thereof, as a nucleophile with a suitable electrophilic group. Alternatively, the hydroxyl groups of the polymeric polyol can be converted into good leaving groups, such as sulfonate esters, and reacted with a functionalizing reagent containing a nucleophilic group.

The functionalizing reagent will typically comprise a reactive group, X, that is either an electrophilic group reactive with a hydroxyl group or anion thereof on the polymeric polyol or, if some or all of the hydroxyl groups of the polyol have been converted to good leaving groups, a nucleophilic group. The functionalizing reagent will also comprise the functional group, Y, that is intended to be covalently attached to the polymer. Optionally, the functionalizing reagent will further comprise a spacer moiety linking the reactive group, X, with the functional group, Y. Exemplary spacer moieties include —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—, —CH$_2$—CH$_2$—C(O)—NH—CH$_2$—, —CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—, —CH$_2$—CH$_2$—C(O)—, —CH$_2$—CH$_2$—CH$_2$—C(O)—, —CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

In one or more embodiments, the functionalizing reagent has the following structure:

$$X—(CR_1R_2)_m—Y \qquad \text{Formula IV}$$

wherein: X is a group reactive with a hydroxyl group or anion thereof, or a good leaving group, in a nucleophilic substitution or nucleophilic addition reaction; R$_1$ and R$_2$ are each independently selected H or alkyl; m is 0-10 (e.g., 0, 1, 2, 3, 4, 5, 6, 7, 8, 9, or 10), preferably 1-3; and Y is a functional group, optionally in protected form, and preferably selected from the group consisting of such as aldehyde hydrate, ketone hydrate, amide, amine, hydrazine, hydrazide, thiol, carboxylic acid, dithiopyridine, vinylpyridine, phenol, and oxime The X reactive group is preferably a good leaving group, such as halogen (e.g., bromo or chloro) or a sulfonate ester (e.g., p-tolylsulfonyl, methylsulfonyl, trifluorosulfonyl, or trifluoroethylsulfonyl), or a substituted or unsubstituted vinyl group. The substituting group or groups attached to the vinyl group carbon atoms are typically alkyl, substituted alkyl, alkoxy, substituted alkoxy, or halogen.

In one or more embodiments, X is halogen, m is 0, and Y is p-tolylsulfonyl, methylsulfonyl, trifluorosulfonyl, or trifluoroethylsulfonyl. Other exemplary functionalizing reagents of Formula IV include X'—(CR$_1$R$_2$)$_m$—C(O)—O—Rp, CH$_2$=CY'—(CR$_1$R$_2$)$_m$—C(O)—O—Rp, X'—(CR$_1$R$_2$)$_m$—Z, CH$_2$=CY'—(CR$_1$R$_2$)$_m$—Z, X'—(CR$_1$R$_2$)$_m$—CN, and CH$_2$=CY'—(CR$_1$R$_2$)m-CN, wherein X' is Br or Cl, Z is an ortho ester, Y' is H, halogen, alkyl, substituted alkyl, alkoxy, or substituted alkoxy, and Rp is alkyl or substituted alkyl. If the functional group, Y, of the functionalizing reagent is in protected form, the method of the invention further comprises deprotecting the functional group. For example, if the Y group is a protected carboxylic acid (e.g., an ortho ester or an alkyl ester), the deprotecting step comprises hydrolysis of the protecting group to form the carboxylic acid. An exemplary protected carboxylic acid group has the structure —C(O)—O—Rp, wherein Rp is an alkyl or substituted alkyl group. Protected carboxylic acids include: esters, such as methyl ester, methoxymethyl ester, methylthiomethyl ester, tetrahydropyranyl ester, benzyloxymethyl ester, phenyacyl ester, n-phthalimidomethyl ester, 2,2,2-trichloroethyl ester, 2-haloethyl ester, 2-(p-toluenesulfonyl)ethyl ester, t-butyl ester, cinnamyl ester, benzyl ester, triphenylmethyl ester, bis(o-nitrophenyl)methyl ester, 9-anthrylmethyl ester, 2-(9,10-dioxo) anthrylmethyl ester, piperonyl ester, trimethylsilyl ester, t-butyldimethylsilyl ester and S-t-butyl ester; thiolesters, such as methylthiol, ethylthiol, phenylthiol, p-snitrophenylthiol, benzylthiol and t-butylthiol; amidates such as O-alkyl-N-alkyl, O-aryl-N-alkyl, O-alkyl-N-aryl, O-aryl-N-aryl, 2-substituted-1-3-oxazolines, 2-substituted-1-3-(4H)-dihydrooxazines; thioamidates, such as S-alkyl-N-alkyl, S-aryl-N-alkyl, S-alkyl-N-aryl, S-aryl-N-aryl, 2-substituted-1,3-thiazolines, 2-substituted-1,3-(4H)-1,3-dihydrothiazines; amides and hydrazides such as N,N-dimethylamide, N-7-nitroindoylamide, hydrazide, N-phenylhydrazide, N,N'-diisopropylhydrazide.

If the Y group is a protected amine (e.g., a carbonitrile group), the deprotecting step can comprise reducing the carbonitrile group to form the amine. Alternatively, one can consider the carbonitrile group as a protected carboxylic acid and deprotection would involve hydrolysis. Protected amines include: carbamates such as 9-fluorenylmethyl, 9-(2-sulfo) fluorenylmethyl, 9-(2,7dibromo)fluorenylmethyl, 17-tetrabenzo[a,c,g,i]fluorenylmethyl, 2-chloro-3-indenylmethyl, benz[f]inden-3-ylmethyl, 2,7-di-t-butyl-[9-(10,10-dioxo-10,10,10,10-tetrahydrothioxanthyl)]methyl, 1,1-dioxobenz[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2' and 4'-pyridyl)ethyl, 2,2-bis(4'-nitrophenyl)ethyl, N-(2-pivaloylamino)-1,1-dimethylethyl, 2-[(2nitrophenyl) dithio]-1-phenylethyl, 2-(N,N-dicyclohexylcarboxamido) ethyl, t-butyl, 1-adamantyl, 2-adamantyl, vinyl, allyl, cinnamyl, 2-3'-pyridyl-prop-2-enyl, 8-quinolyl, N-hydroxypiperidinyl, alkyldithio, p-methoxybenzyl, p-nitrobenzyl, p-chlorobenzyl, 2,4-dichlorobenzyl, 4-methylsulfinylbenzyl, 9-anthrylmethyl, diphenylmethyl, 2-methylthioethyl, 3-methylsulfonylethyl, 2-(p-toluenesulfonyl) ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 2,5-dimethoxybenzyl, 1-methyl-1-(3,5-dimethoxyphenyl)ethyl, α-methylnitropiperonyl, o-nitrobenzyl, and 3,4-dimethoxy-6-nitrobenzyl; urea type derivatives such as phenothiazinyl-(10)-carbonyl derivative, N'-p-toluenesulfonylaminocarbonyl, N'-phenylaminothiocarbonyl; amides such as N-formyl, N-chloroacetyl, N-trichloroacetyl, N-trifluoroacetyl, N-phenylacetyl, N-3-phenylpropionyl, N-4-pentenoyl, N-picolinoyl, N-3-pyridylcarboxamido, N-benzoylphenylalanyl derivative, N-p-phenylbenzoyl, N-o-nitrophenylacetyl, N-o-nitrophenoxyacetyl, N-3-(o-nitrophenyl)propionyl, N-2-methyl-2-(o-nitrophenoxy)propionyl, N-3-methyl-3-nitrobutyryl, N-o-nitrocinnamoyl, N-o-nitrobenzoyl, N-3-(4-t-butyl-2,6-dinitrophenyl)2,2-dimethylpropionyl, N-o-(benzoyloxymethyl) benzoyl, N-2-methyl-2-(o-phenylazophenoxy)propionyl, N-4-chlorobutyryl, N-acetoacetyl, N-3-(p-hydroxyphenyl) propionyl, (N'-dithiobenzyloxycarbonylamino)acetyl, N-acetylmethionine derivative, and 4,5-diphenyl-3-oxazolin-2-one; cyclic imide derivatives such as N-phthaloyl, N-tetrachlorophthaloyl, N-4-nitrophthaloyl, N-dithiasuccinoyl, N-2,3-diphenylmaleoyl, N-2,5-dimethylpyrrolyl, N-2,5-bis(triisopropylsiloxy)pyrrolyl, N-2,5-bis(triisopropylsiloxy)pyrrolyl, N-1,1,4,4-tetramethyldisilyazacyclopenane adduct, N-1,1,3,3-tetramethyl-1,3-disilaisoindolyl, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl, 1,3,5-dioxazinyl. These and other protective groups are described in detail in Greene et al., supra.

As noted above, in one or more embodiments, the hydroxyl groups of the polyol, or some fraction thereof, are converted to a good leaving group prior to reaction with the functionalizing reagent. For example, the hydroxyl groups can be converted to a leaving group of structure —Z, wherein Z is halogen or a sulfonate ester, by reacting the polyol with a reagent having, for example, the structure X'—SO$_2$—R$_3$, wherein R$_3$ is alkyl or substituted alkyl and X' is Br or Cl. Preferred R$_3$ groups include p-tolyl, methyl, trifluoromethyl, and trifluoroethyl. In this embodiment, the conversion of the hydroxyl groups to good leaving groups can serve as the controlling step used to produce the desired disparity in concentration between the monosubstituted polymer product and the multisubstituted polymer species. For instance, the reaction to convert the hydroxyl groups to good leaving groups can be performed under conditions effective to form no more than about 25 percent of the disubstituted polymer (i.e., the polymer species having two hydroxyl groups converted to leaving groups) and typically no more than about 12 percent of the disubstituted polymer. In certain embodiments, no more than about 8 percent, preferably no more than about 5 percent, more preferably no more than about 2 percent, and most preferably no more than about 1 percent of the disubstituted polymer is formed. The reaction converting hydroxyl groups to leaving groups typically results in a ratio of monosubstituted polymer to disubstituted polymer of about 2:1 to about 40:1, preferably about 4:1 to about 20:1, more preferably about 10:1 to about 18:1.

D. Optional Alkylation Step

If a monofunctional, end-capped polymer is desired, the process of the invention can include an alkylation step, either prior to or after the above-described functionalizing reaction. Preferably, the alkylation step occurs after the functionalizing reaction so that the alkylation reaction can be allowed to go to completion without the need to control the reaction stoichiometrically as described more fully below. Typically, the alkylation step will occur before any deprotecting step, if needed.

If the alkylation step is conducted prior to the functionalizing reaction, then the alkylating reaction becomes the controlling reaction step that determines the ratio of the monosubstituted polymer to the disubstituted polymer products. In this embodiment, the polyol starting material is subjected to an alkylating step, thus forming a mixture comprising an unalkylated polymer, a monoalkylated polymer comprising a single alkoxy group, and a dialkylated polymer comprising two alkoxy groups, under conditions effective to form at least about 25 mol percent of the dialkylated polymer. This polymer mixture is then reacted with a functionalizing reagent as described above to form a mixture comprising an unalkylated polymer comprising two Y groups, a monoalkylated polymer comprising a single Y group, and a dialkylated polymer comprising no Y groups. This polymer mixture can then be purified to provide a monoalkylated, monofunctional polymer substantially free from the unalkylated and dialkylated polymer species. In certain embodiments, the alkylation reaction is allowed to proceed until at least about 25 mol percent of dialkylated polymer is produced, preferably at least about 65 mol percent, more preferably at least about 40 mol percent, and still more preferably at least about 90 mol percent.

The alkylation step converts hydroxyl groups to alkoxy groups of formula —OR', wherein R' is an alkyl or substituted alkyl group, such as $C_1$-$C_{20}$ alkyl, substituted $C_1$-$C_{20}$ alkyl, $C_1$-$C_{20}$ alkylene-aryl, and substituted $C_1$-$C_{20}$ alkylene-aryl. Preferred R' groups include methyl, ethyl, propyl, butyl, pentyl, hexyl, and benzyl.

Preferably, the alkylation reaction comprises treating the polymeric polyol (if the alkylation step occurs prior to functionalization) or the polymeric mixture (if the alkylation step occurs after functionalization) with any known alkylating agent in the art, such as dialkylsulfate, alkyl sulfonates (such as alkyl p-toluenesulfonate, alkyl methanesulfonate, alkyl trifluoromethylsulfonate, and alkyl trifluoroethylsulfonate), diazoalkane, alkyl halide, N,N'-dimethylformamide dialkyl acetal, 3-alkyl-1-p-tolyltriazene, trimethylanilinium hydroxide, trialkyloxonium fluoroborate, trimethylsulfonium hexafluorophosphonate, or alkyl triciloroacetimidate.

D. Exemplary Reaction Schemes

To further illustrate certain embodiments of various aspects of the invention, exemplary reaction schemes are provided below. These schemes are meant to be representative; details for the following particular transformations and purifications are provided in the Examples section. The schemes provided below can be extended to any of the polymers, functionalizing reagents, leaving groups, protecting groups, and purification modes described herein.

Scheme I demonstrates the use of PEG diol as a starting material (rather than mPEG) to prepare a monofunctionalized mPEG. The introduction of an ionizable group, in this case a carboxyl, renders the PEG material suitable for an ion exchange chromatographic separation as described in detail herein, to provide monofunctional mPEG that is essentially free of diol and diol-derived impurities. Generally speaking, the purified monofunctionalized polymers of the invention, whether end-capped or not, contain less than 0.3 wt % of a difunctional polymer. The purified mPEG monofunctionalized material, depending upon the nature of the functional group, is of a purity suitable for conjugation to a protein, small molecule, surface, or the like, or for any other pharmaceutical application, or may be further functionalized to prepare a desired polymer reagent.

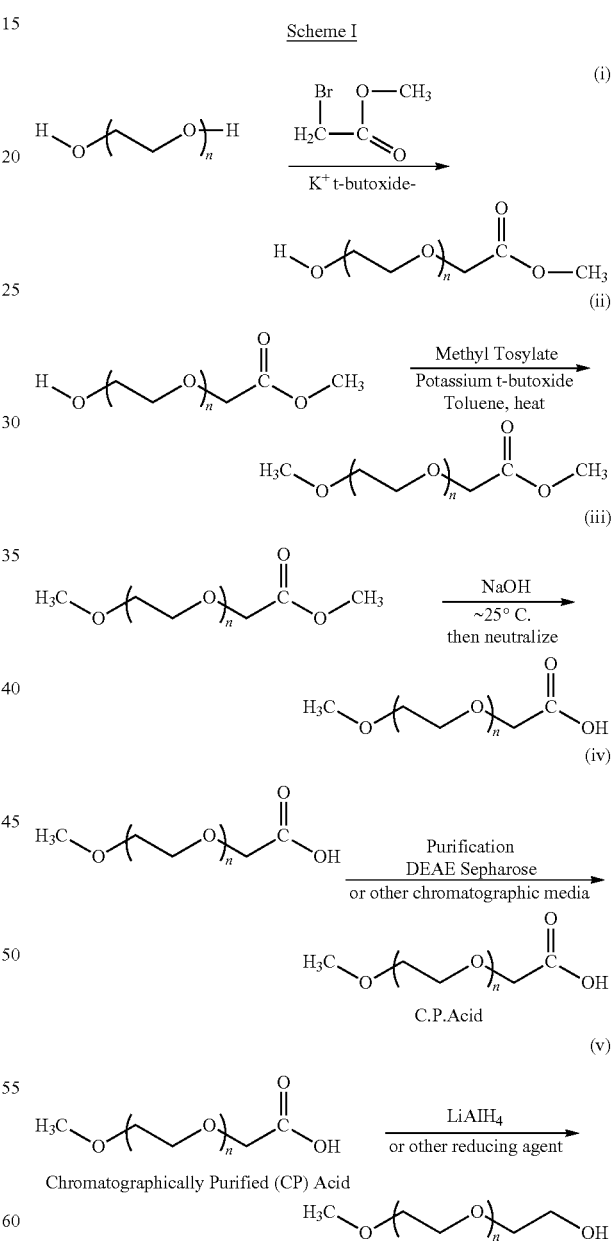

Scheme I

In Scheme I, PEG diol is used as a starting material. In I(i), the PEG diol is functionalized using an exemplary functionalizing agent, bromo-acetic acid methyl ester. The functionalizing reagent reacts with the anionic form of the PEG diol to displace the halogen, and form the corresponding methylene methyl ester. As illustrated in Scheme I(i), one of the PEG hydroxyl groups is converted to the corresponding methylene methyl ester. Although shown as a simple reaction scheme in which only one terminus of the polymer is functionalized, as has been described in great detail herein, the product of the functionalization reaction is really a mixture of unsubstituted PEG diol starting material, the desired mono-substituted PEG-OH product, and the disubstituted PEG ester. The progress of the reaction can be monitored to ensure the reaction is stopped or quenched at the desired time, although using a known amount of starting materials and a limited-amount of the functionalizing reagent will stop the reaction automatically as a result of exhaustion of the functionalizing reagent. Again, routine experimentation will provide the amount of functionalizing reagent that results in the desired amounts of products.

With reference to FIG. 1, it can be seen that formation of 25% monosubstituted product corresponds to about 72% unreacted PEG diol and about 3% disubstituted product. Upon formation of 50% monosubstituted PEG product (the maximum amount of monosubstituted product that can be formed from diol starting material), the crude product mixture contains 25% of each PEG diol and PEG disubstituted product. FIG. 1 also demonstrates that as the amount of disubstituted PEG product in the reaction mixture exceeds 25%, the amount of monosubstituted product concomitantly decreases. Thus, the reaction ends (e.g., as a result of depletion of functionalizing reagent) or is quenched upon formation of 25% or less disubstituted product. The progress of the reaction can be monitored using any one of a number of analytical techniques, such as $^1$H NMR or HPLC.

In returning to Scheme I, in I(ii), the hydroxyls in the PEG mixture from I(i), namely those present in the PEG diol starting material and the monosubstituted product, are methylated with a protecting group, e.g., tosylate or any other suitable protecting group, followed by conversion of the functional group, in this case a methyl ester, to an ionizable group, —COOH, designated generally herein as Y. The use of methyl as an alkylating group is preferred when mPEG functional materials are desired. At this point, the reaction mixture contains neutral dimethoxy PEG (resulting from the alkylation step), monofunctional mPEG, $CH_3O(CH_2CH_2O)_n$—$CH_2COOH$ (also referred to as "mPEG carboxymethyl acid"), and difunctional PEG, $HOOCCH_2(OCH_2CH_2)_n$ $OCH_2COOH$, also referred to as "bis-carboxymethyl PEG"). The mixture is then purified to remove neutral PEG, which is nominally dimethoxy PEG but potentially with neutral impurities such as PEG diol or mPEG-OH and difunctional PEG. While any of a number of suitable purification techniques may be employed, generally, chromatography is preferred, and in particular, ion exchange chromatography. The separation of PEG diol (optionally in it alkylated form, typically referred to herein as neutral PEG) and disubstituted PEG (also referred to herein as difunctional PEG) from the desired monofunctional material is preferably done in a sequential fashion.

In Scheme I, the purified acid is then reduced to the corresponding alcohol to provide mPEG-OH that is extremely pure, that is to say, which, in some cases contains less than 1% diol. Although lithium aluminum hydride is shown as the reducing agent, any suitable reducing agent can be used. Examples include sodium borohydride, sodium cyanoborohydride, $H_2$/palladium, lithium triethylborohydride, HI, alkali metals in liquid ammonia, and zinc with acid or base. In some cases, the amount of diol or difunctional material present in the purified material is below current limits of detection. Although Scheme I illustrates reduction of the carboxylic acid to the corresponding alcohol to provide mPEG-OH of ultra-high purity, this transformation is meant to be illustrative, and any of a number of alternative subsequent transformations of the polymer acid may be carried out.

Scheme I can also be referred to when considering this aspect of the invention more generally. Moreover, detailed descriptions of the variables and examples thereof are extendable to every aspect of the invention to which they apply. For instance, any water-soluble non-peptidic polymer can be used in place of PEG. Such a polymer is represented generally as HO-POLY-OH, where POLY is the water-soluble and non-peptidic polymer portion of the molecule. Although not shown in Scheme I, the method may optionally include a step wherein the hydroxyl groups in the polymer diol are converted to a better leaving group, Z. Leaving groups include halogens such as iodide, bromide, and chloride, as well as sulfonate esters, —$N_2^+$. Preferred leaving groups are groups that are better leaving groups than —OH. As previously described for methylating PEG in FIG. 1, the conversion to a better-leaving group produces a mixture of products, unreacted, unsubstituted polymer diol starting material, mono-substituted polymer having a single Z group, HO-POLY-Z; and disubstituted polymer comprising two Z groups, Z-POLY-Z. Again, such transformations are typically carried out under conditions effective to form no more than about 25 percent of the disubstituted polymer.

In a subsequent step, the polymer diol (or the polymer mixture produced in an optional preceding step to convert hydroxyls to leaving groups) is reacted, in one or more reaction steps, with a functionalizing reagent. The functionalizing reagent reacts with the polymer in a nucleophilic substitution or nucleophilic addition reaction. The functionalizing reagent is useful for introducing into the polymer a functional group, most preferably an ionizable group, or a precursor to an ionizable group, or an ionizable group in protected form.

In one or more particular embodiments, the functionalizing reagent comprises the structure X-L-Y, wherein X is a group that allows the functionalizing reagent to react with the polymer in a nucleophilic addition or substitution reaction. Preferably, X is a group that reacts with a hydroxyl, optionally in anionic form, or with a carbon atom to which the hydroxyl is attached, or is displaced by a hydroxyl. L is an optional linker that is interposed between X and Y. $L_0$ indicates the absence of a linker and $L_1$ indicates the presence of a linker, and L encompasses both. Preferably L is hydrolytically stable, and is made up of inert or non-reactive atoms or groups of atoms each of the moieties described above with respect to the spacer moiety describe above can be an L.

In one or more embodiments, L has a structure —$(CR_1R_2)_m$—, where $R_1$, in each occurrence, is independently H or an organic radical selected from the group consisting of alkyl, substituted alkyl, alkenyl, substituted alkenyl, alkynyl, substituted alkynyl, aryl, and substituted aryl; and $R_2$, in each occurrence, is independently H or an organic radical selected from the group consisting of alkyl, substituted alkyl, alkenyl, substituted alkenyl, alkynyl, substituted alkynyl, aryl, and substituted aryl, and m ranges from 0-15. For example, m may be 0, 1, 2, 3, 4, 5, 6, 7, 8, 9, 10, 11, 12, 13, 14, 15. In one or more embodiments, $R_1$ and $R_2$ are each independently H or alkyl, and m ranges from 0-10. Typically, the alkyl group is straight chain lower alkyl or branched lower alkyl such as methyl, ethyl, propyl, isopropyl, n-butyl, isobutyl, sec-butyl, pentyl, etc., with straight chain being generally preferred. One particularly preferred alkyl substituent is methyl. In one or more embodiments thereof, $R_1$ and $R_2$ are each independently H or lower alkyl. In yet one or more additional embodiments, $R_1$ and $R_2$ are each H, and m is 1, 2, 3, 4, 5, 6, 7, 8, 9, or 10. In addition, L can be —(CR$_1$R$_2$)$_m$— where R$_1$ on the carbon proximal to Y is alkyl, and in all other occurrences, R$_1$ and R$_2$ are H. In one particular embodiment of the preceding, R$_1$ is methyl or ethyl or propyl. Alternatively, L is —(CR$_1$R$_2$)$_m$— where R$_1$ on the carbon beta to Y is alkyl, preferably methyl or ethyl or propyl of isopropyl, and in all other occurrences, R$_1$ and R$_2$ are H. Although any of the exemplary spacer moieties described supra can be an L moiety, preferred L moieties in some embodiments possess a structure selected from —CH$_2$—, —CH$_2$—CH$_2$—, —CH$_2$—CH$_2$—CH$_2$—, —CH$_2$—CH(CH$_3$)—, —CH$_2$—CH(CH$_2$CH$_3$)—, —CH(CH$_3$)CH$_2$—, —CH$_2$—CH(CH$_3$)—CH$_2$—, —CH$_2$—CH$_2$—CH$_2$—CH$_2$—, —CH$_2$—CH$_2$—CH$_2$—CH(CH$_3$)—, —CH$_2$—CH$_2$—CH(CH$_3$)—CH$_2$—, —CH$_2$—CH(CH$_3$)—CH$_2$—CH$_2$—, —CH(CH$_3$)—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—.

Preferably, Y is an ionizable functional group. Ionizable functional groups are particularly well suited for the chromatographic purifications of the invention, and can be exploited as a means to separate unsubstituted, monosubstituted, and disubstituted polymer species contained in a mixture. Relative amounts of the various polymer species are ideally carried through the various transformations, thereby forming a mixture comprising a neutral polymer of formula HO-POLY-OH, a monosubstituted polymer of formula HO-POLY-L-Y, and a disubstituted polymer of formula Y-L-POLY-L-Y, where ideally, no more than about 25 percent of the disubstituted polymer species relative to the other polymer species is present.

Optionally, the method may further comprise alkylating the polymer mixture produced in either the first or second steps to convert the remaining hydroxyl groups to alkoxy groups. Thereafter, the resulting polymer mixture can be purified using, for example, ion exchange chromatography, to provide a substantially pure monosubstituted polymer comprising a single -L-Y group, and in the case where an alkylation has been conducted, to provide a substantially pure monosubstituted methoxy-terminated polymer.

Scheme II provides another representative embodiment of the method of the invention. In Scheme II, PEG diol is first methylated to provide a polymer mixture as previously described (II(i)). The alkylated polymer mixture is then reacted with a functionalizing agent, in this case, 1-(3-bromopropyl)-4-methyl-2,6,7-trioxa-bicyclo[2.2.2]octane (II(ii)). As can be seen, the functionalizing agent possesses a group, in this case, Br$^-$, that is displaced by the counter anion of hydroxide. The Br$^-$ is an example of the variable, X. The functionalizing agent also contains Y, in this case a protected carboxylic acid. Specifically, Y is an ortho ester, 4-methyl-2,6,7-trioxabicyclo[2.2.2]octane, but can be any carboxyl protecting group. The linker portion, L, in the functionalizing agent, is —(CH$_2$)$_2$—. The protecting group is then removed, in this instance by hydrolysis, to produce a PEG carboxylic acid (II(iii)). As described previously, although shown as the mPEG-acid, the mPEG acid is really present in a mixture comprising neutral PEG, dimethoxy PEG, the desired monofunctional mPEG-acid, as well as the difunctional material, HOOC—CH$_2$CH$_2$—(OCH$_2$CH$_2$)$_n$—O—CH$_2$CH$_2$COOH. The monofunctional PEG carboxylic acid is then purified, e.g., by ion exchange chromatography. Scheme II can also be modified to conduct the alkylation step following the introduction of the ortho ester (i.e., after reaction with the functionalizing reagent).

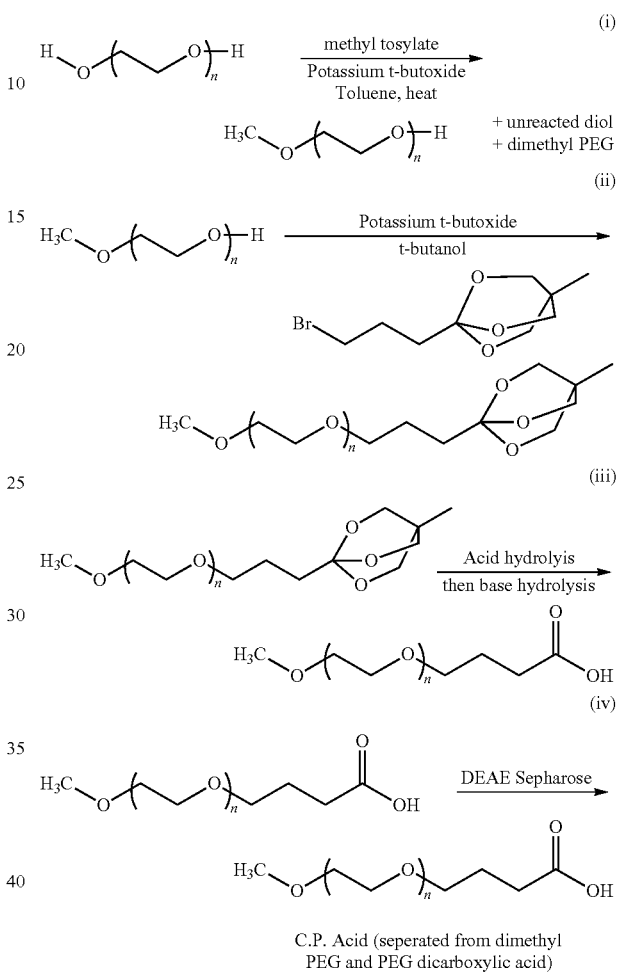

C.P. Acid (seperated from dimethyl PEG and PEG dicarboxylic acid)

In illustrative Scheme III below, a Michael-type addition reaction is used to functionalize a PEG diol by introduction of a carbonitrile group. Generally speaking, the functionalizing reagent in the method of the invention in this instance is a Michael type reagent. In (III(iii)), the functionalizing reagent is a carbonitrile. In this case, the functionalizing agent contains a functional group, Y, where Y is a nitrile, and is part of a Michael type reagent. The nitrile is a precursor to an ionizable group. In Scheme III, X is —CH$_2$, and the linker, L, in the polymer nitrile product mixture is —CH$_2$CH$_2$—. The nitrile is then reduced to an amine using a reducing agent, e.g., H$_2$ over a metal catalyst such as rhodium-containing catalysts, nickel, palladium or platinum. Scheme II demonstrates a diol as the precursor for the Michael addition reaction, however, if desired, the PEG diol can first be alkylated, or alternatively, can be alkylated subsequent to the Michael addition. The polymer amine-mixture is then purified, e.g., by ion exchange chromatography. Introduction of an ionizable group such as an amine makes this approach particularly suitable for an ion exchange-based separation to yield essentially pure monoamine, absent neutral and disubstituted polymer species.

Scheme III

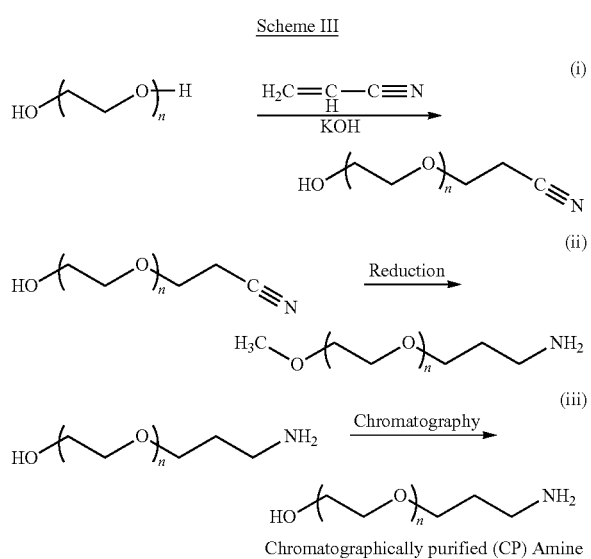

Chromatographically purified (CP) Amine

Other Michael-type reagents can be substituted for the carbonitrile shown in Scheme III. For example, the following reagents can be used as Michael Type reagents,

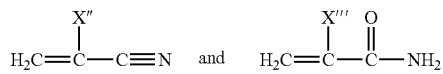

wherein X" is halo or alkyl and X''' is H, halo, or alkyl.

The CP amine shown in Scheme III can be used to prepare a variety of heterobifunctional derivatives by further functionalizing either the amino terminal or the terminal —OH group. Moreover, by using a chromatographically purified material such as the CP amine, any such heterobifunctional polymer prepared therefrom will be essentially free of polymeric contaminants such as the neutral and disubstituted polymer species described herein.

One such representative reaction scheme is provided as Scheme IV below. In Scheme IV, the CP amine from Scheme III is converted into a maleimide by transformation of the amino group. This synthetic approach is advantageous since maleimide-terminated polymers are particularly useful for conjugation to thiol-containing moieties, such as the cysteines in proteins. Moreover, the heterobifunctional maleimide amino-terminated polymer can then be further transformed, if desired, by further functionalization at the hydroxyl terminus.

Scheme IV

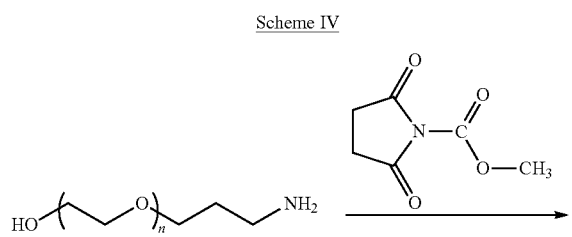

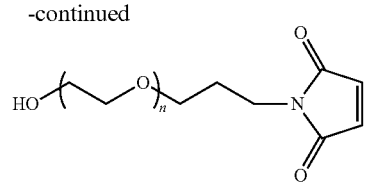

In Scheme IV, the CP amine is converted to the maleimide by reaction with N-methoxycarbonylmaleimide 2,5-dioxo-2,5-dihydro-pyrrole-1-carboxylic acid methyl ester. Additional maleimidyl polymer derivatives that can be prepared from the chromatographically purified starting materials described herein, as well as methods that can use the chromatographically purified starting materials described herein, are disclosed in U.S. Pat. No. 6,602,498, the contents of which are incorporated herein by reference. This reaction approach can be employed with any chromatographically purified polymer amine prepared by the methods described herein. Again, as with all of the illustrative schemes herein, the scheme below is applicable to any of the herein described polymers, functionalizing reagents and purified monofunctional polymers.

In Scheme IV (as well as each of Schemes I, II, III and V), (n) is a positive integer, typically in at least one of the following ranges: from 2 to 3,000; from 10 to 2,000; and from 100 to 1000. In addition, each hydrogen of the hydroxyl groups shown in Scheme IV can optionally be an organic radical, typically an alkyl (such as lower alkyl) including benzyl. The amine terminated polymer in Scheme IV is a useful starting material to form the polymeric reagent bearing a terminal maleimidic group (as shown in Scheme IV) that can be used, for example, in a conjugation reaction with a biologically active protein.

Scheme V represents yet another particular embodiment of the method of the invention. Generally, hydroxyls on a polymer diol (or on an end-capped polymer alcohol) are first transformed to a better leaving group. An exemplary leaving group shown here is mesylate or methanesulfonyl, although any suitable leaving group may be used. In the first step of this approach, conversion is preferably held to about 20% so as to reduce the ultimate amount of difunctional amine formed. Again, although a single monofunctionalized polymer species is shown in V(i), the monofunctionalized polymer is really present in a reaction mixture containing unreacted starting material and polymer di-mesylate. The polymer mesylate, HO—POLY-Ms, can then be reacted with a variety of different functionalizing agents. In this approach, the functionalizing reagents react with the polymer via a nucleophilic substitution reaction, such that the —OMs group on the polymer is displaced. In reaction V(ii-a), the functionalizing reagent can be described generally as X-L-Y, where X is —O, L is —(CH$_2$)$_3$—, and Y is —NH$_2$. In reaction V(ii-b), the functionalizing reagent is ammonia, which again acts to displace —OMs. The third reaction V(ii-c) illustrates a functionalizing reagent having a four carbon linker rather than a three carbon linker as in V(ii-a). Each of these reaction mixtures is particularly suited for purification by ion exchange chromatography as described herein, to provide essentially pure monofunctionalized, monosubstituted polymers. These polymers may be used directly, e.g., to prepare functionalized active agents, hydrogels, or any other such suitable application, or may be further functionalized as described above.

Scheme V

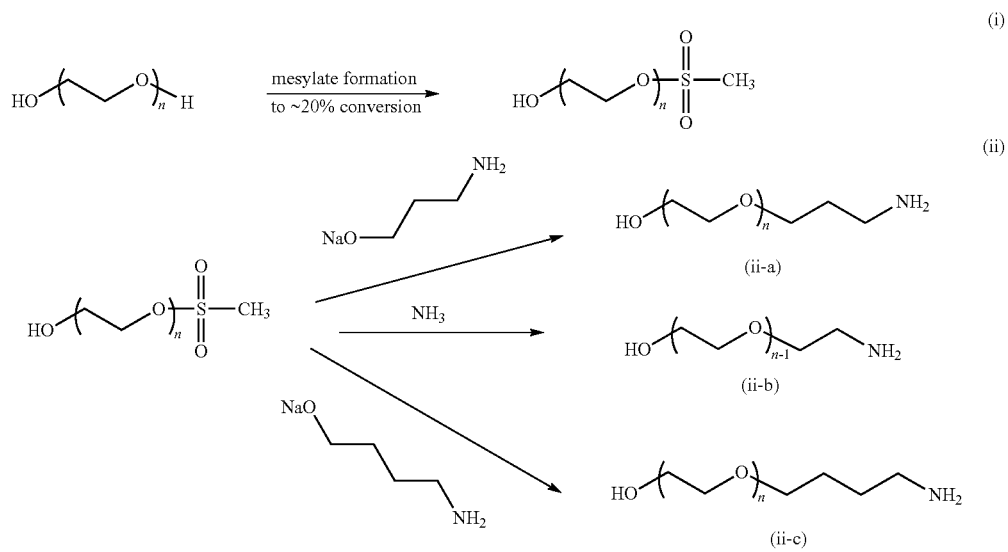

E. Purification Step

The process of functionalizing a polymer diol or polyol starting material results in a mixture of products, including a monosubstituted polymer and one or more multisubstituted polymer species (e.g., a disubstituted polymer). Thus, in order to make the method of invention of the utmost practical utility, the product polymer mixture is purified to separate the monosubstituted polymer from the di- or multi-substituted polymer, as well as any remaining unreacted polymer diol, polyol, or other neutral polymer species. Any of a number of purification techniques can be used.

In a preferred embodiment of the invention, in particular where the polymer mixture contains polymer species having ionizable functional groups, ion exchange chromatography is employed to separate the various polymer constituents of the product mixture based on their differences in charge. In one aspect, the present invention provides an improved ion exchange chromatography approach that overcomes the problems associated with other commonly employed, e.g., gradient, ion exchange methods used to separate polymers. This process is referred to as gradient polymer elution chromatography, and differs from the method of the invention in many respects.

Gradient based chromatography involves changing the ionic strength of the mobile phase or eluent to drive differently charged molecules off an ion exchange column at different intervals. Generally, in a gradient chromatography, a gradient is applied that changes from a poor or low eluting strength solvent to a good or high eluting strength solvent, based upon the relative affinity of the column versus the mobile phase for a particular polymer.

In a typical gradient separation, a sample is applied to a column and a low eluting strength solvent is employed, so as not to allow any separation to occur initially. Rather, the mixture components are collected at the top of the column, in a concentrating step. The gradient is then progressed and the ionic strength of the solvent is gradually increased until "good" or high eluting strength solvent conditions are achieved such that sample components begin their separation and begin to migrate. Charged substances are separated via column materials carrying an opposite charge. Species with a higher charge are bound to an ion exchange column more strongly, while the less highly charged species elute more rapidly. The strength of the eluent is typically altered by changing pH, buffer, and/or salt concentration (ionic strength). Techniques that rely upon gradient separation are tedious, time-consuming, use large volumes of solvent, and require analysis of multiple fractions. Thus, gradient type methods are poorly suited for commercial-scale processes. Moreover, gradient-based separation techniques also rarely achieve high purity levels of any given polymer (e.g., in reference to the number of various polymer species present and the polydispersity of the purified polymer product), particularly when separating higher molecular weight polymer species.

The ion exchange separation process of the invention provides superior separation and purification of polymer mixtures that contain multivalent anions or cations. More specifically, the method is well suited for polymer mixtures that contain uncharged and charged substances differing in charge, e.g., polymer that are uncharged, singly charged, doubly charged, triply charged, and so on (that is, to say, two or more species having ionizable groups that under certain pH conditions, carry different charges). One such example is a polymer mixture containing a neutral polymer (i.e., a polymer diol or polyol or a mono- or di-alkylated polymer absent an ionizable functional group), a monosubstituted polymer having a single ionizable group, such as an amine or carboxylic acid group, and a di- or multi-substituted polymer having two or more ionizable functional groups. Separation is achieved by relying upon differences in charge, and, in certain embodiments, differences in molecular weight. Rather than eluting species having different charges from a single column (or a number of single column chromatograph separations) by changing the ionic strength of the eluate in a stepwise, gradient fashion, the present method involves the use of discrete columns and discrete eluates. Generally, a solvent having a constant or static concentration as it is fed into a column is used. That is to say, the solvent feed as is enters the column is of a constant, non-gradient composition. The ionic strength and/or pH of the solvent is adjusted to suit the polymer species being eluted from the column.

Specifically, the method of the invention involves the use of more than one ion exchange column to achieve ultra high purity mono-substituted polymers, e.g., typically containing less than 0.3% by weight difunctionalized or multi-functionalized polymer impurities.

The first column(s) or pre-column(s) are sized to adsorb substantially all, and most preferably, all, of the disubstituted polymer and other multisubstituted polymer species that are present in a polymer mixture. Typically, determination of an appropriate size for the first column(s) or pre-column(s) involves the step of establishing column capacity. Column capacity is experimentally determined and typically involves passing a solution containing an excess amount of standard solution of one type of species of polymer [e.g., a solution of $HO(O)CH_2O-(CH_2CH_2O)_n-CH_2C(O)OH$ or $H_2N-CH_2CH_2CH_2O-(CH_2CH_2O)_n-CH_2CH_2CH_2-NH_2$] known to adsorb to the stationary phase. This standard is added so as to saturate the column, often verified by detecting the polymer species in the eluate retrieved from the column. Thereafter, any nonadsorbed species are washed out of the column, typically by passing distilled water through the column. Next, all polymer species adsorbed on the column are eluted (generally by means of passing a salt solution), extracted with organic solvent and then weighed after removal of solvent. This amount corresponds to the column capacity. To the extent that two or more columns are provided in series, the overall column capacity of the system is equivalent to the added column capacities of the individual columns.

Having established column capacity, only column(s) sufficiently sized to adsorb substantially all of the di- or multi-substituted polymer species (e.g., disubstituted polymer, polymer species comprising two $-L_{0,1}-Y$ groups, or difunctional polymer) desired to be removed form a mixture will be used in an initial purification step. A column is sufficiently sized in this regard when it has a column capacity greater than the amount of the di- or multisubstituted polymer species to be retained from a mixture. As discussed previously, the amount of the polymer species in any mixture can be determined by analyzing a sample of the mixture, by having reference to FIG. 1., or any other art-known method.

Thus, the column capacity of pre-column(s) used in a first eluting step can be one or more of at least a 10%, at least a 20%, at least a 30%, at least a 40%, at least a 50%, at least a 60%, at least a 70%, at least a 80%, at least a 90%, at least a 100%, and at least a 110% increase of the total amount of the polymer species in the mixture to be purified. For example, with respect to a first step in a method for purifying of a mixture containing 5 g of disubstituted polymer, a first ion exchange column having capacity to adsorb 10 g of the disubstituted polymer can be used (thereby representing 100% increase of the total amount of the difunctional polymer species to be adsorbed on the first column). In addition, a mixture containing 25 g of disubstituted polymer, a first ion exchange column having capacity to adsorb 35 g of the disubstituted polymer can be used (thereby representing a 40% increase of the total amount of the polymer species to be adsorbed on the first column).

With respect to the second column(s) or main column(s) used in the purification step, it is sufficient to have a column capacity substantially equivalent to the amount of monofunctional polymers within the polymer species to be retained from the mixture (e.g., monosubstituted polymer, polymer species comprising one $-L_{0,1}-Y$ groups, or monofunctional polymer). Second or main column(s) having greater column capacities can also be used to prevent any losses of monofunctional polymer(s).

Having identified appropriate columns, purification can take place. Advantageously, the polymer mixture equilibrates with the solid phase media in the precolumn as the mixture flows through the column to allow the strongest binding material (e.g., those species bearing the greatest number of the charges to which the column is directed) to be retained. Slower rates of adding the mixture correspond to an increased extent of equilibration.

In one or more embodiments, a plurality of "precolumns" (e.g., 2, 3, or 4 precolumns) connected in series is used to remove the multisubstituted polymer species, the plurality of precolumns being sized to collectively adsorb all of the disubstituted polymer and other multisubstituted polymer species. Typically, some amount of monosubstituted polymer species will be adsorbed as well, but to a lesser extent since only one ionized species is associated with the monosubstituted polymer species.

Advantageously, the purification method does not require the use of a distillation step to concentrate solutions such as the eluate. Furthermore, the purification method described herein is suited to purify not only relative small molecular weight polymers (e.g., 2,000 Da), but can be used to purify molecular weight polymers having higher molecular weights as well. Thus, the purification method is suited for purifying molecular weights in the following ranges: from about 100 Da to about 180,000 Da; from about 3,000 Da to about 120,000 Da; from about 5,000 Da to about 100,000 Da; from about 8,000 Da to about 100,000 Da; from about 10,000 Da to about 100,000 Da; from about 12,000 Da to about 80,000; and from about 15,000 Da to about 80,000 Da. In addition, the equipment used in the purification process does not rely on gradients, thereby reducing the need for obtaining many very diluted eluate fractions, which, in turn, requires a multitude of collection vessels. Furthermore, the present method uses substantially less volumes of eluent compared to prior art methods, typically on the order of less than about 50% eluent, preferably less than about 75% eluent, more preferably less than about 85% eluent, still more preferably less than about 90% eluent, with eluent amounts of less than about 95% relative to prior art methods being most preferred. Consequently, the methods described herein require only a single collection vessel, and do not require a distillation step to concentrate eluate to enable extraction of purified product. In addition, the apparatuses described herein do not require more than a single collection vessel and do not require a means for distillation.

The eluate from the first column, which contains the mono-substituted polymer and the neutral polymer, is then passed through the second (or main) ion exchange column or columns connected in series. The monosubstituted polymer is absorbed onto the second (or main) column(s), which are sized in order to retain preferably all of the monosubstituted polymer. The neutral polymer passes through all of the columns and can be collected and possibly recycled for reuse in the method of the invention. It is generally preferred to wash each column with a solution having low ionic strength (e.g., deionized water) to remove any remaining neutral polymer thereon.

Solutions having the requisite low ionic strength for any particular system are known to those having ordinary skill in the art. In addition, solutions having the requisite low ionic strength can be determined through routine experimentation by passing a candidate solution (typically, although not necessarily, a very weak salt solution or buffered solution)

through column(s) known to have both charged and neutral polymer species contained therein, collecting the candidate solution that has passed through the column(s), and then testing the collected solution for the presence of any charged polymer species. A candidate solution having passed through the column(s) with no or substantially no (e.g., less than 1%) charged polymer species content represents a solution having a low ionic strength for that particular system.

Retrieval of charged polymer species (whether they be singly charged polymer species or di- or multiply charged polymer species) adsorbed onto the ion exchange columns is typically requires desorbing. Desorption typically involves passing salt solution having high ionic strength through the column(s), thereby desorbing charged polymer species. For instance, the second (or main) column(s) containing monosubstituted polymer can be washed with a salt solution having high ionic strength, such as a NaCl solution, to remove and collect a substantially pure monosubstituted polymer product.

Salt solutions having the requisite high ionic strength for any particular system are known to those having ordinary skill in the art. In addition, solutions having the requisite high ionic strength can be determined through routine experimentation by passing a candidate solution through the column(s) having a known amount of charged polymer species adsorbed therein, collecting the candidate solution that has passed through the column(s), and then testing the collected solution for the presence of charged polymer species. A candidate solution having passed through the column(s) with at least about 85%, more preferably at least about 90%, still more preferably at least about 95%, and most preferably at least about 99% of the known amount of charged polymer species contained therein represents a solution having a high ionic strength for that particular system. This procedure can be used to identify a solution having sufficient ionic strength so that the solution will desorb difunctional polymer through the first column or precolumn.

Since the differently charged polymer species have been separated by adsorption on separate columns, there is no need to use a salt solution gradient to recover each polymer species separately. Instead, a salt solution having a constant ionic strength can be used to elute the desired product from each column.

If desired, the multisubstituted polymer species absorbed on the precolumn(s) can also be collected by passing a salt solution through the precolumn to drive desorption of the polymer. Typically, the precolumn(s) are sized so as to ensure absorption of all of the multisubstituted polymer in the feed stream, meaning that some monosubstituted polymer will also be absorbed on the precolumn. Thus, purity of the multisubstituted product eluate is typically lower as compared to the monosubstituted product eluted from the one or more additional columns. Preferably, the product eluted from the precolumn(s) contain no more than about 70 weight percent monosubstituted polymer, more preferably no more than about 50 weight percent, and most preferably no more than about 30 weight percent. If the product eluted from the precolumn(s) contain multiple multicharged polymer species (e.g., doubly-charged and triply-charged), then a second pass through the ion exchange system can be used to further separate the polymer mixture by retaining the higher charged species in the precolumns (e.g., the triply-charged species) and retaining the less highly charged species (e.g., doubly-charged) in the second column.

Analytical determination, using an HPLC column that responds to both charge and molecular weight, can be used to determine how much of each species is present in a sample, both before being run through a column and after. By "substantially pure" is meant that the monosubstituted polymer contains less than about 5 weight percent polymer impurities, such as multisubstituted polymer or unsubstituted (i.e., neutral) polymer, preferably less than about 3 weight percent, more preferably less than about 2 weight percent, and most preferably less than about 1 weight percent. A preferred composition will comprise monomethoxy end-capped poly(ethylene glycol) ("mPEG-OH"), wherein the composition has a poly(ethylene glycol) diol content of less than 0.3 wt. %.

If it is desired to narrow the molecular weight range (i.e., polydispersity) of the monosubstituted polymer product, a series of two or more columns (e.g., 2, 3, 4, 5, 6, 7, 8, 9, or 10 columns) following the precolumn can be used to attenuate the molecular weight range of the monosubstituted polymer absorbed on each column. Monosubstituted polymer of smaller molecular weight will absorb first, meaning the average molecular weight of the polymer material absorbed on each successive column will increase. Thus, by increasing the number of columns, one can not only separate the monosubstituted polymer from the higher charged species, but also lower polydispersity. In certain embodiments, the polydispersity of the monosubstituted polymer is reduced by at least about, 0.01 preferably at least about 0.02, more preferably at least about 0.03, and most preferably at least about 0.05. In an alternative embodiment, if lower molecular weight monosubstituted polymer is the desired product, one can simply undersize the second or main column such that all of the monosubstituted polymer cannot be adsorbed thereon. Since lower molecular weight species will selectively bind first, the desired lower molecular weight monosubstituted polymer will absorb on the column. In addition or alternatively, one can use several columns and collect lower molecular weight monofunctional polymer from the first column in the series of columns following the precolumn.

If the original polymer mixture that is subjected to functionalization contains a relatively small amount of polyol, such as in the case of a polymer starting material comprising an impure mPEG (e.g., an mPEG contaminated with less than about 20% by weight PEG diol), then the resulting polymer mixture requiring purification may contain no neutral polymer or only a negligible amount of neutral polymer if the functionalization reaction is allowed to proceed to completion. In this case, the ion exchange purification system can comprise only a single column sized to absorb all of the multifunctional polymer species (i.e., a precolumn). The eluate from the precolumn will then contain only the desired monofunctional product.

Following purification, if desired, the substantially pure monosubstituted polymer can be further modified to convert the ionizable functional group to a second functional group, such as hydroxyl, active ester, active carbonate, ortho ester, acetal, aldehyde, aldehyde hydrates, ketone, ketone hydrate, alkenyl, acrylate, methacrylate, nitrile, primary or secondary amide, imide, acrylamide, active sulfone, amine, hydrazide, thiol, carboxylic acid, isocyanate, isothiocyanate, maleimide, substituted succinimide, vinylsulfone, dithiopyridine, vinylpyridine, amidate, 2-substituted-1,3-oxazoline, 2-substituted 1,3-(4H)-dihydrooxazines, 2-substituted-1,3-thiazoline, 2-substituted 1,3-(4H)-dihydrothiazines, hydroxylamine, iodoacetamide, epoxide, glyoxal, dione, mesylate, tosylate, and tresylate.

During the ion exchange process, the eluate from each column can be monitored using techniques known in the art, such as by measuring the conductivity of the eluate, analyzing the eluate by ion exchange chromatography, size exclusion chromatography, high performance liquid chromatography, or thin layer chromatography, or by detecting the presence of PEG in the eluate by treating a drop of eluate with a drop of 1% polyacrylic acid (Aldrich, Mn 250,000) in 1 N HCl ("PAA test"). Presence of PEG is indicated by the immediate appearance of a white precipitate of PEO/PAA complex. This test is very specific to the polyether backbone of PEG and not influenced by end group modifications of the polymer, molecular weight, or the presence of inorganic ions in the analyzed solution. Monitoring of the eluate streams is particularly important during the washing step to determine when substantially all of the neutral polymer has been removed from the columns.

As would be understood in the art, the ion exchange columns utilized in the present invention can be any ion exchange columns conventionally used to separate a mixture based on charge (Ion Exchange Chromatography. Principles and Method. Pharmacia Biotech 1994; "Chromatography: a laboratory handbook of chromatographic and electrophoretic techniques." Heftman, E (Ed.), Van Noostrand Rheinhold Co., New York, 1975). Each column comprises an ion exchange media and a mobile phase, or eluent, that passes through the ion exchange media. Ion exchange columns suitable for use in the present invention include POROS® ion exchange media made by Applied Biosystems and SEPHAROSE® ion exchange media made by Pharmacia.

The ion exchange media, which is typically a polymeric resin (e.g., dextran, agarose, cellulose, styrene-divinylbenzene copolymer) containing charged groups, is selected based on a number of factors, including the charge and pKa value of the ionizable functional group present on the polymers to be separated. Typically, the ion exchange media is selected so as to provide a sufficient difference in pKa value between the ionizable functional group and the ion exchange media to favorably drive absorption of the polymer, preferably a difference of at least 4-5 units. As would be understood, the ion exchange media will comprise negatively charged groups (i.e., a cation exchanger) if the ionizable functional group is positively charged and will comprise positively charged groups (i.e., an anion exchanger) if the ionizable functional group is negatively charged. Exemplary negatively charged groups that may be used include carboxymethyl (CM), sulphopropyl (SP), and methyl sulphonate (S). Exemplary positively charged groups include triethylammoniumethyl (TMAE), diethylaminoethyl (DEAE), quaternary aminoethyl (QAE), and quaternary ammonium (Q). Typically, the media in each column will be the same, but different media could be used in each column without departing from the present invention.

A two column embodiment of the ion exchange system of the invention is shown in FIG. 2. As shown, the ion exchange system 10 comprises a feed tank or vessel 12 that contains a supply of the solution of the crude polymer mixture to be separated. Typically, the polymer mixture will be dissolved in deionized water or a neutral aqueous solution having very low ionic strength. As noted above, the polymer mixture will often include a neutral or unsubstituted polymer species, such as a polymer having the structure HO-POLY-OH or R'O-POLY-OR', a monosubstituted polymer of formula HO-POLY-L-Y or R'O-POLY-L-Y, and a disubstituted polymer of formula Y-L-POLY-L-Y, wherein Y, R', L, and POLY are as defined above.

The feed tank 12 is in fluid communication with a first ion exchange column or precolumn 16 sized to trap higher charged species (i.e., a disubstituted polymer). The outlet of the precolumn 16 is in fluid communication with the inlet of the second or main ion exchange column 18, which is appropriately sized to retain all of the monocharged polymer species. The outlet of each column is in fluid communication with one or more product recovery or receiving vessel 20, each vessel adapted to receive eluate from one or more of the columns. The salt solutions and neutral solutions used to wash the columns and/or recover the absorbed polymer species can be housed in one or more solvent vessels 22, which are in fluid communication with the inlet of one or more of the columns.

FIG. 3 illustrates an embodiment comprising a precolumn 16 and a plurality of second or main columns 18 that can be used to narrow the molecular weight range of the desired monosubstituted polymer product as explained above.

F. Exemplary Products

As previously discussed, the methods described herein can be used in the preparation of substantially pure polymeric reagents. Examples of such products existing as substantially pure compositions with little or no poly(ethylene glycol) diol species include the following:

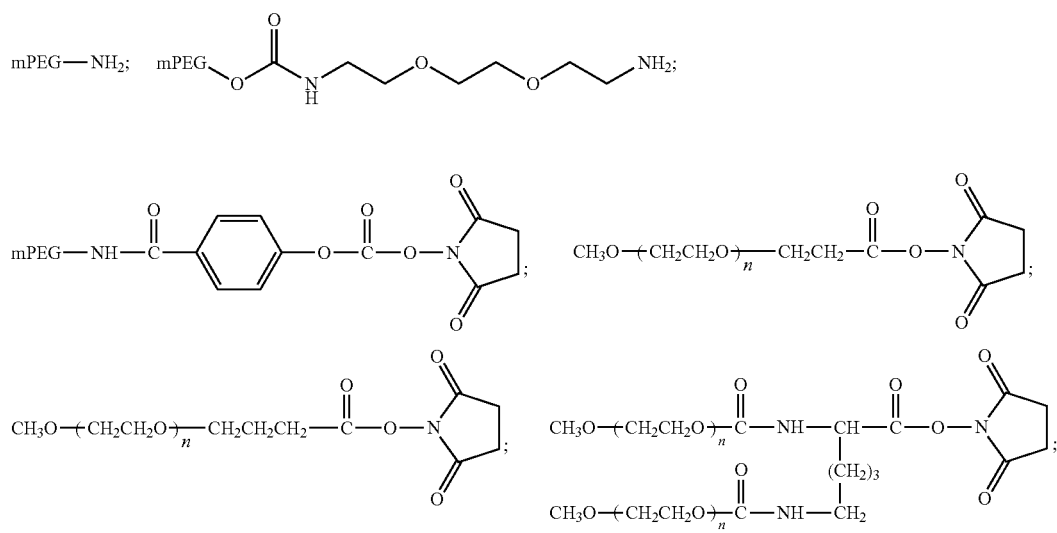

-continued
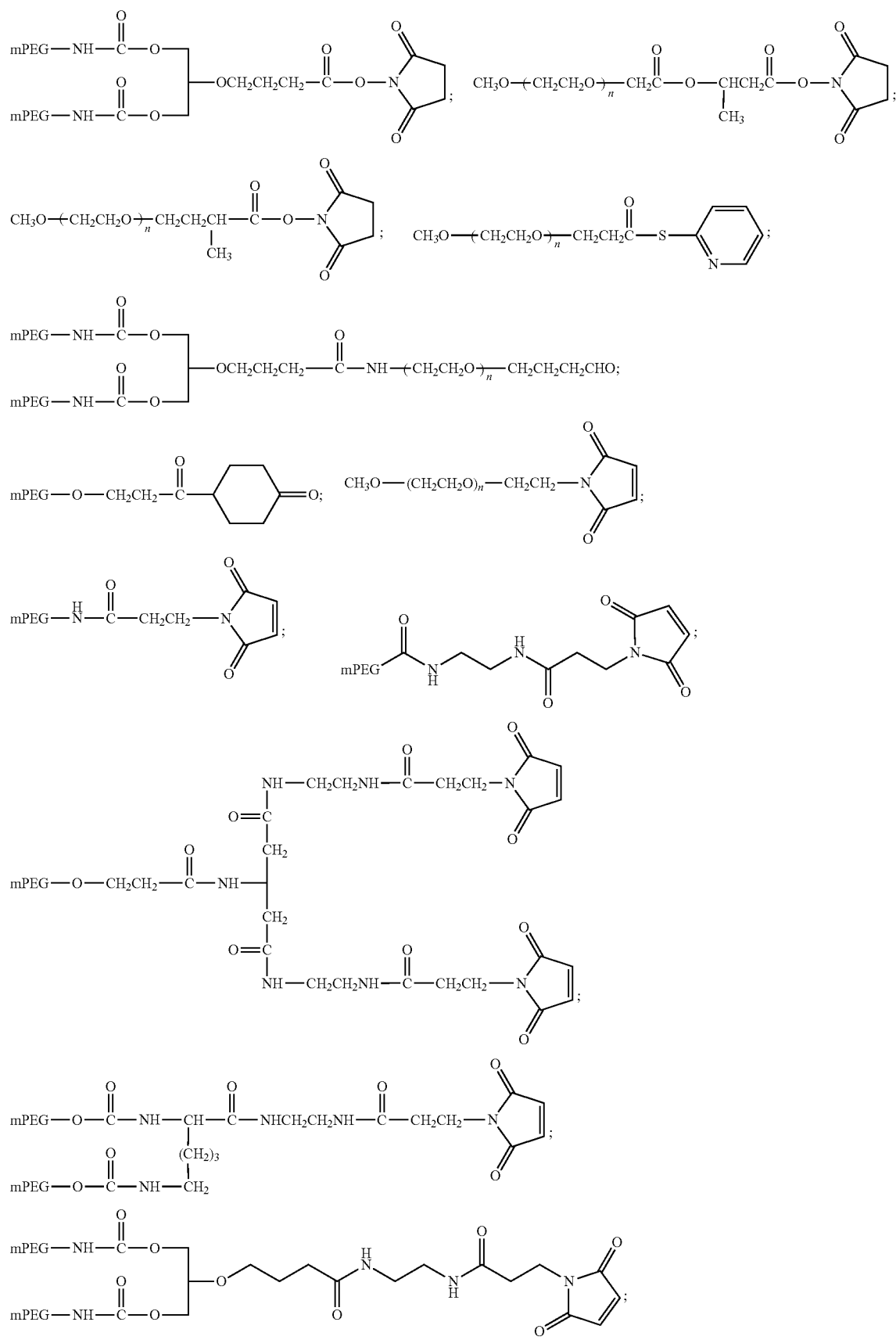

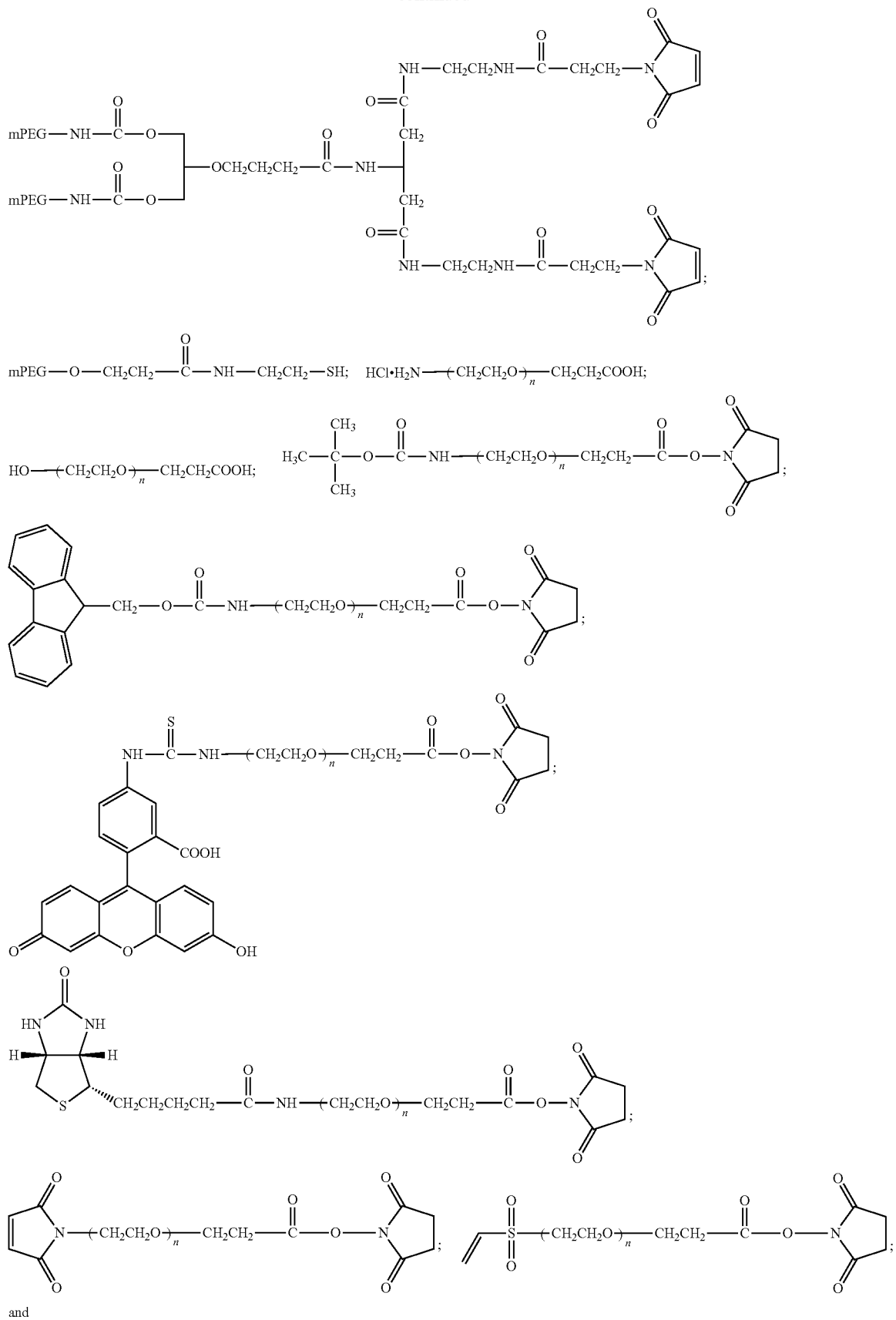

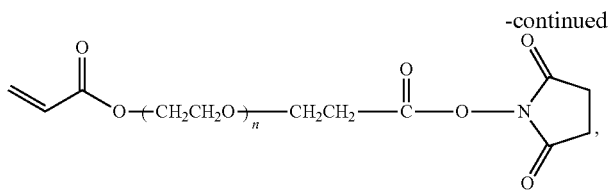

-continued wherein (n) is a positive integer, typically falling within at least one of the following ranges: from 2 to 3,000; from 10 to 2,000; from 100 to 1,000, and each mPEG is $CH_3-(OCH_2CH_2)_n-$, wherein (n) is a previously defined.

The corresponding functional group with optional spacer moiety (e.g, $L_{0,1}$-Y) are evident from the above exemplary polymeric structures.

All articles, books, patents, patent publications and other publications referenced herein from the incorporated by reference in their entireties.

III. EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

All PEG reagents referred to in the appended examples are commercially available unless otherwise indicated, e.g., from Nektar Therapeutics, Huntsville, Ala. All $^1$HNMR data was generated by a 300 or 400 MHz NMR spectrometer manufactured by Bruker. High Performance Liquid Chromatography (HPLC) was performed using Agilent 1100 HPLC system (Agilent), gel permeation or ion exchange column, aqueous phosphate buffer as a mobile phase, and refractive index (RI) detector

Example 1 mPEG (20,000 Da)-Butanoic Acid

A. 4-Bromobutyrate ester of 3-methyl-3-hydroxymethyloxetane (MW=251.12)

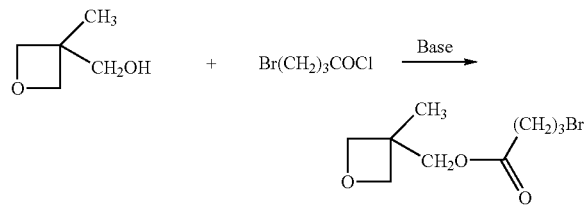

3-Methyl-3-hydroxymethyloxetane (10.2 g, 0.1 mole) [Sigma-Aldrich Corporation of St. Louis, Mo.] was dissolved in anhydrous dichloromethane (200 ml) and pyridine (9.8 ml, 0.12 moles) was added. The solution was cooled to 0 C and 4-bromobutyryl chloride (18.5 g, 0.1 mole) [Sigma-Aldrich Corporation of St. Louis, Mo.] dissolved in anhydrous dichloromethane (50 ml) was added dropwise over 20 minutes. The mixture was stirred overnight under an argon atmosphere. Next, the reaction mixture was washed with water and dried with anhydrous magnesium sulfate. The solvent was then distilled off under reduced pressure. Yield 23.6 g. NMR ($d_6$-DMSO): 1.26 ppm (s, 3H), 2.07 ppm (m, 2H), 2.51 ppm (t, 2H), 3.56 ppm (t, 2H), 4.14 ppm (s, 2H), 4.24 ppm (d, 2H), 4.38 ppm (d, 2H).

B. 1-(3-Bromopropyl)-4-methyl-2,6,7-trioxabicyclo [2,2,2]octane (MW=251.12)

(4-Bromobutanoic acid OBO ester)

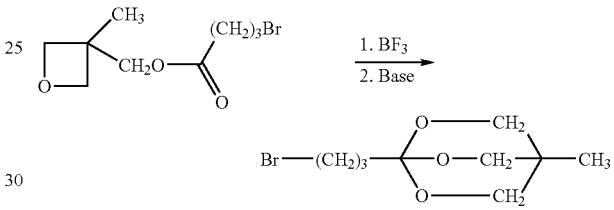

Crude 4-bromobutyrate ester of 3-methyl-3-hydroxymethyloxetane (20.1 g, 0.08 moles) was dissolved in anhydrous dichloromethane (100 ml), the solution was cooled to 0° C. and boron trifluoride diethyl etherate (2.5 ml, 0.022 moles) was added. The mixture was stirred for 4 hours at 0° C. Triethylamine (12 ml) was added, the mixture was stirred for 15 minutes, and the solvent was distilled off under reduced pressure. The crude product was dissolved in ethyl ether (180 ml) and the solution was filtered to remove the solid impurities. Next, ether was distilled off and the product was distilled under reduced pressure (kugelrohr, 110-115° C., 0.05 mm Hg). Yield 15.0 g. NMR ($d_6$-DMSO): 0.74 ppm (s, 3H), 1.68 ppm (m, 2H), 1.88 ppm (m, 2H), 3.52 ppm (t, 2H), 3.81 ppm (s, 6H).

C. PEG(20,000 Da)-Butanoic Acid

A solution of commercially available PEG (Mn=20,300 Da, polydispersity 1.040) (50.0 g, 0.005 equivalents) in toluene (300 ml) was azeotropically dried by distilling off 50 ml toluene. 1.0M solution of potassium tert-butoxide in tert-butanol (5.0 ml, 0.005 moles) and 1-(3-bromopropyl)-4-methyl-2,6,7-trioxabicyclo[2,2,2]octane (0.65 g, 0.0025 moles) were added and the mixture was stirred overnight at 70° C. under an argon atmosphere. Next, 1.0M solution of potassium tert-butoxide in tert-butanol (18.0 ml, 0.018 moles) and methyl p-toluenesulfonate (4.4 g, 0.0239 moles) were added and the mixture was stirred overnight at 45° C. under an argon atmosphere. The solvent was distilled off under reduced pressure and the residue was dissolved in distilled water (450 ml). The pH of the solution was adjusted to 2 with 5% phosphoric acid and the solution was stirred for 15 minutes at room temperature. Next, the pH was readjusted to 12 with 1M sodium hydroxide and the solution was stirred for 2 hours keeping the pH at 12 by periodic addition of 1M sodium hydroxide. The pH was adjusted to 3 with 5% phosphoric acid and the product was extracted with dichloromethane. The extract was dried with anhydrous magnesium sulfate and added to ethyl ether. The precipitated product was filtered off and dried under reduced pressure. Yield 44.7 g. NMR ($d_6$-DMSO): 1.72 ppm (q, $\underline{CH_2}$—$CH_2$—COO—) 2.24 ppm (t, —$\underline{CH_2}$—COO—), 3.24 ppm (s, —$OCH_3$), 3.51 ppm (s, PEG backbone).

D. Purification

The product from (C) above was determined to be a mixture of polymer species. An HPLC chromatogram revealed that the polymer mixture product from C included PEG(20,000 Da)-dibutanoic acid (26.1%), mPEG(20,000 Da)-butanoic acid (50.4%), and PEG(20,000 Da) dimethyl ether (23.5%). A purification was carried out in accordance with the invention to obtain purified mPEG(20,000 Da)-butanoic acid.

The above mixture of products from C was dissolved in distilled water (4470 ml) and the resulting solution was passed through a first chromatographic column (precolumn) filled with 300 ml of anion exchange gel: DEAE SEPHAROSE® Fast Flow (Pharmacia). This amount of anion exchange gel was only able to retain about 35% of PEG acids present in the polymer mixture from step C. Column capacity was previously determined in small scale laboratory experiments. The anion exchange chromatogram revealed that the eluate contained only mPEG(20,000 Da)-butanoic acid and PEG(20,000 Da) dimethyl ether. PEG(20,000 Da)-dibutanoic acid and a portion of mPEG(20,000 Da)-butanoic acid were absorbed by the gel in the precolumn.

Next the eluate collected from the precolumn was applied to a second column (main column) containing 1000 ml of DEAE SEPHAROSE® Fast Flow gel. The amount of anion exchange gel in the column was sufficient to retain all mPEG (20,000 Da)-butanoic acid present in the eluate from the first column. Column capacity was previously determined in small scale laboratory experiments. An anion exchange chromatogram showed that the eluate from the second or main column contained only PEG(20,000 Da) dimethyl ether. Anion exchange chromatography showed that the only polymer adsorbed on the second column was mPEG(20,000 Da)-butanoic acid, which was eluted using 5% NaCl solution (1500 ml).

The pH of the eluate from the second or main column was adjusted to 3 by addition of 5% phosphoric acid and the product was extracted with dichloromethane. The extract was dried over anhydrous magnesium sulfate, the drying agent removed, and the dried solution was added to ethyl ether to precipitate the purified product. The precipitated product was filtered off and dried under reduced pressure. Yield 14.4 g. NMR ($d_6$-DMSO): 1.72 ppm (q, $\underline{CH_2}$—$CH_2$—COO—) 2.24 ppm (t, —$\underline{CH_2}$—COO—), 3.24 ppm (s, —$OCH_3$), 3.51 ppm (s, PEG backbone).

Anion exchange chromatography: mPEG(20,000 Da)-butanoic acid 100%. (no other polymer species detected). Gel permeation chromatography: Mn=20,700 Da, polydispersity 1.010.

The product eluted from the first column (precolumn) contained both some mPEG(20,000 Da)-butanoic acid and the PEG(20,000 Da)-dibutanoic acid.

Example 2 mPEG (20,000 Da)-Amine

A solution of commercially available PEG (Mn=20,300 Da) (50.0 g, 0.005 equivalents) in toluene (300 ml) was azeotropically dried by distilling off 50 ml toluene. Dichloromethane (60 ml), triethylamine (1.40 ml, 0.0100 moles), and methanesulfonyl chloride (0.35 ml, 0.00452 moles, 90.4% of stoichiometric amount) were added and the mixture was stirred overnight at room temperature under argon atmosphere. The mixture was filtered and the solvents were distilled off under reduced pressure. The residue was dissolved in anhydrous toluene (250 ml) and sodium methoxide (25% solution in methanol, 23.0 ml) was added. The mixture was stirred overnight at 70° C. under an argon atmosphere, filtered and the solvents were distilled off under reduced pressure. The crude product was dissolved in 500 ml distilled water. NaCl (40 g) was added and the pH of the solution was adjusted to 7.2 with 5% phosphoric acid. The product was extracted with dichloromethane. The extract was dried over anhydrous magnesium sulfate, filtered, and the solvent was distilled off under reduced pressure. Yield 43.3 g. NMR analysis showed that 79% of PEG-OH groups were converted to PEG-$OCH_3$ groups.

The obtained partially methylated PEG(20,000 Da) (20.0 g) was dissolved in toluene (150 ml) and the solution was azeotropically dried by distilling off 50 ml of toluene. Dichloromethane (25 ml), triethylamine (0.60 ml), and methanesulfonyl chloride (0.30 ml) were added and the mixture was stirred overnight at room temperature under n argon atmosphere. The mixture was filtered and the solvents were distilled off under reduced pressure. The product was then dissolved in dichloromethane (30 ml) and 500 ml of isopropyl alcohol was added. The precipitated product was filtered off and dried under reduced pressure giving 19.5 g of product. NMR analysis showed that the product contained 79% of PEG-$OCH_3$ groups and 21% of PEG-methanesulfonate groups.

The product was then dissolved in 350 ml of ammonium hydroxide (30%) and the solution was stirred for 70 hours at room temperature. The resulting mixture of methoxy-PEG-amine products was extracted with dichloromethane. The extract was dried with anhydrous magnesium sulfate and the solvent was distilled off under reduced pressure. The product was re-dissolved in dichloromethane (30 ml) and precipitated with 500 ml of isopropyl alcohol. Yield 15.2 g.

Analysis of relative proportions of polymer species by cation exchange chromatography: PEG(20,000 Da)-diamine 4.7%, mPEG(20,000 Da)-amine 30.4%, PEG(20,000 Da) dimethyl ether 64.9%.

The above mixture was dissolved in distilled water (1500 ml) and the resulting solution was passed through a first chromatographic column (precolumn) filled with 40 ml of cation exchange resin POROS® 50 HS (Applied Biosystems). This amount of cation exchange gel was only able to retain about 10% of PEG amines present in the polymer mixture. Column capacity was previously determined in small scale laboratory experiments.

Cation exchange chromatography showed that the eluate from the precolumn contained only mPEG(20,000 Da)-amine and PEG(20,000 Da) dimethyl ether. PEG(20,000 Da)-diamine and part of mPEG(20,000 Da)-amine were adsorbed by the resin in the precolumn.

Next, the eluate from the precolum was applied to the second column (main column) containing 300 ml of POROS® 50 HS resin. The amount of cation exchange gel in the column was sufficient to retain all mPEG(20,000 Da)-amine present in the eluate from the first column. Column capacity was previously determined in small scale laboratory experiments. Cation exchange chromatography showed that the eluate from the second (or main) column contained only PEG(20,000 Da) dimethyl ether, leaving solely the desired monofunctionalized polymer on the second (or main) column. The mPEG(20,000 Da)-amine, adsorbed on the second (or main) column, was then eluted using a 5% NaCl solution (600 ml).

The pH of the second (or main) column eluate was adjusted to 11 with 0.5 M sodium hydroxide and the product was extracted with dichloromethane. The extract was dried over anhydrous magnesium sulfate, filtered, and added to ethyl ether. The precipitated product was isolated by filtration and dried under reduced pressure. Yield 3.1 g.

NMR ($d_6$-DMSO): 2.64 ppm (t, —$CH_2$—$NH_2$), 3.24 ppm (s, —$OCH_3$), 3.51 ppm (s, PEG backbone).

Analysis by cation exchange chromatography revealed that the collected, dried product contained 100% m-PEG(20,000 Da)-amine, free from detectable amounts of neutral or difunctionalized polymer.

Example 3 mPEG (20,000 Da)-Carboxylic Acid, Sodium Salt

A solution of commercially available PEG (Mn=20,300 Da, polydispersity 1.040) (50.0 g, 0.005 equivalents) in toluene (300 ml) was azeotropically dried by distilling off 50 ml toluene. Dichloromethane (60 ml), triethylamine (1.30 ml, 0.0093 moles), and methanesulfonyl chloride (0.30 ml, 0.00388 moles, 77.5% of stoichiometric amount) were added and the mixture was stirred overnight at room temperature under an argon atmosphere. The mixture was filtered and the solvents were distilled off under reduced pressure. The residue was dissolved in anhydrous toluene (250 ml) and sodium methoxide (25% solution in methanol, 21.0 ml) was added. The mixture was stirred overnight at 70° C. under an argon atmosphere. The mixture was then filtered and the solvents were distilled off under reduced pressure. The crude product was dissolved in 500 ml distilled water, NaCl (40 g) was added and the pH of the solution was adjusted to 7.2 with 5% phosphoric acid. The product was extracted with dichloromethane. The extract was dried with anhydrous magnesium sulfate and the solvent was distilled off under reduced pressure. Yield 44.1 g. NMR analysis showed that 66% of PEG-OH groups were converted to PEG-$OCH_3$ groups.

The partially methylated PEG (20,000 Da) (40.0 g) obtained above was dissolved in toluene (150 ml) and the solution was azeotropically dried by distilling off 50 ml of toluene. Next a 1.0M solution of potassium tert-butoxide in tert-butanol (8.2 ml, 0.0082 moles, 6.0 fold excess) was added to the above reaction mixture. Ethyl bromoacetate (1.13 ml, 0.0102 moles, 7.5 fold excess) was then added and the mixture was stirred overnight at 50° C. under an argon atmosphere. The solvent was distilled off under reduced pressure and the residue was dissolved in distilled water (500 ml). The pH of the solution was adjusted to 12.10 with 1M sodium hydroxide and the solution was stirred overnight, keeping the pH at 12.10 by periodic addition of 1M sodium hydroxide. The pH was adjusted to 1.0 with 1M hydrochloric acid and the product was extracted with dichloromethane. The extract was dried with anhydrous sodium sulfate, concentrated, and added to ethyl ether. The precipitated product was filtered off and dried under reduced pressure. Yield 34.7 g. NMR ($d_6$-DMSO): 3.21 ppm (s, —$OCH_3$), 3.51 ppm (s, PEG backbone), 4.01 ppm (s, —$CH_2$—COO—).

Analysis by anion exchange chromatography: PEG(20,000 Da)-dicarboxylic acid (11.5%), mPEG(20,000 Da)-carboxylic acid (45.0%), PEG(20,000 Da) dimethyl ether (43.5%). NMR analysis showed that the product contained 66% of PEG-$OCH_3$ groups and 34% of PEG-carboxylic acid groups.

The above mixture was dissolved in distilled water (3500 ml) and the resulting solution was eluted through the first chromatographic column (precolumn) packed with 200 ml of anion exchange gel: DEAE SEPHAROSE® Fast Flow (Pharmacia).

Anion exchange chromatographic analysis revealed that the eluate contained only mPEG(20,000 Da)-carboxylic acid and PEG(20,000 Da) dimethyl ether. All of the PEG(20,000 Da)-dicarboxylic acid and part of the mPEG(20,000 Da)-carboxylic acid were adsorbed (retained) by the gel in the precolumn.

Next, the solution was applied to the second column (main column) containing 800 ml of DEAE SEPHAROSE® Fast Flow gel. Anion exchange chromatography revealed that the eluate from the column contained only PEG(20,000 Da) dimethyl ether. The mPEG(20,000 Da)-carboxylic acid, adsorbed (retained) on the column, was eluted using 5% NaCl solution (1100 ml).

The pH of the eluate was then adjusted to 7 and the product was extracted with dichloromethane. The extract was dried with anhydrous magnesium sulfate and added to ethyl ether to precipitate the purified monocarboxylic acid polymer. The precipitated product was filtered off and dried under reduced pressure. Yield 13.2 g. NMR ($d_6$-DMSO): 3.21 ppm (s, —$OCH_3$), 3.51 ppm (s, PEG backbone), 4.01 ppm (s, —$CH_2$—COO—).

Anion exchange chromatography revealed the recovered product to be 100% mPEG(20,000 Da)-carboxylic acid, without any detectable amounts of PEG(20,000 Da) dimethyl ether or PEG(20,000 Da)-dicarboxylic acid.

Example 4

Diol-free mPEG-20,000 Da mPEG(20,000 Da)-carboxylic acid, sodium salt, (10.0 g, 0.00050 moles) was dissolved in 150 ml toluene and the solvent was distilled off to remove traces of water. The dried product was dissolved in anhydrous tetrahydrofuran (100 ml) at 40-45° C. and lithium aluminum hydride (1.0M solution in tetrahydrofuran, 1.5 ml, 0.0015 moles) was added.

The mixture was stirred at 45° C. overnight under argon atmosphere. Ethyl acetate (0.5 ml) was added, the mixture was stirred 30 min, then the mixture was cooled to about 30° C. and water (0.06 ml) was added and the mixture was stirred 10 min. Next sodium hydroxide (15% solution in water, 0.06 ml) was added, the mixture was stirred 10 min, and finally water (0.18 ml) was added, the mixture was stirred 15 min, and then was filtered to remove precipitated aluminum salt. To the filtrate, isopropyl alcohol (500 ml) was added, and the precipitated product was filtered off and dried under reduced pressure. Yield 8.7 g. NMR ($d_6$-DMSO): 3.21 ppm, (s, 3H, —$OCH_3$); 3.51 ppm (s, PEG backbone); 4.57 ppm (t, 1H, —OH).

HPLC analysis showed that the product is 100% pure mPEG-20,000 Da and free of diol. Gel permeation chromatography: Mn=20,800 Da, polydispersity 1.018.

Example 5

PEG (10,000 Da)-α-hydroxy-ω-propylamine

A mixture of PEG of molecular weight 10,000 Da (20.0 g; 0.00400 equivalents), distilled water (20.0 g) and potassium hydroxide (0.4 g) was cooled to 0-5° C. in an ice bath. Acrylonitrile (0.5 g; 0.00942 moles) was added slowly, and the solution was stirred for 2 hours at 0-5° C. NaCl (2 g) was added and the pH of the solution was adjusted to 7.0 with phosphoric acid. Next, the reaction product was extracted with dichloromethane and the solvent was distilled off under reduced pressure giving 18.7 g of white solid product. NMR analysis showed that the product contained 75% of PEG-OH groups and 25% of PEG-OCH$_2$CH$_2$CN groups. The product was dissolved in 150 ml of ethyl alcohol and palladium catalyst (10 wt % on activated carbon; 2 g) was added. The mixture was hydrogenated at 65° C. under 800 psi of hydrogen. The mixture was then filtered and the solvent was removed under vacuum giving 16.4 g of white product. NMR analysis showed that the product contained 77% of PEG-OH groups and 23% of PEG-OCH$_2$CH$_2$CH$_2$NH$_2$ groups.

Analysis by cation exchange chromatography: PEG(10,000 Da)-dipropylamine 5.3%, PEG (10,000 Da)-α-hydroxy-ω-propylamine 35.4%, and PEG(10,000 Da) 59.3%.

The above mixture was dissolved in distilled water (1500 ml) and the resulting solution was filtered through a first chromatographic column (precolumn) filled with 30 ml of cation exchange resin POROS® 50 HS (Applied Biosystems).

Cation exchange chromatographic analysis showed that the filtrate contained only PEG (10,000 Da)-α-hydroxy-ω-propylamine and PEG(10,000 Da). All of the PEG(10,000 Da)-dipropylamine and part of the PEG (10,000 Da)-α-hydroxy-ω-propylamine were adsorbed (retained) by the resin in the precolumn.

Next, the solution was applied to the second column (main column) containing 250 ml of POROS® 50 HS resin. Cation exchange chromatography showed that the eluate from the column contained only PEG(10,000 Da). PEG (10,000 Da)-α-hydroxy-ω-propylamine, adsorbed on the column, was then eluted using 5% NaCl solution (350 ml). The pH of the eluate was adjusted to 11 with 0.5 M sodium hydroxide and the product was extracted with dichloromethane. The extract was dried with anhydrous magnesium sulfate and added to ethyl ether. The precipitated product was filtered off and dried under reduced pressure. Yield 4.6 g. NMR (d$_6$-DMSO): 1.76 ppm (m, —CH$_2$CH$_2$NH$_2$), 2.80 ppm (t, —CH$_2$—NH$_2$), 3.51 ppm (s, PEG backbone), 4.58 ppm (t, —OH).

Cation exchange chromatography: PEG (10,000 Da)-α-hydroxy-ω-propylamine 100%.

Example 6

PEG (10,000 Da)-α-hydroxy-ω-propylmaleimide

PEG (10,000 Da)-α-hydroxy-ω-propylamine from the Example 5 (4.0 g, 0.0004 moles) was dissolved in saturated aqueous solution of NaHCO$_3$ (30 ml) and the mixture was cooled to 0° C. N-methoxycarbonylmaleimide (0.3 g) was added with vigorous stirring. After stirring for 10 minutes, water (10 ml) was added and the mixture was stirred an additional 50 minutes. The pH was adjusted to 3.0 with 0.5 N sulfuric acid and about 15 wt % NaCl was added. The reaction product was extracted with dichloromethane, the extract was dried with anhydrous magnesium sulfate, and the solvent was distilled off under reduced pressure to dryness. The crude product was dissolved in 6 ml of dichloromethane and precipitated with 100 ml of isopropyl alcohol giving 3.6 g of white powder after drying under reduced pressure. NMR (d$_6$-DMSO): 1.88 ppm (m, —CH$_2$CH$_2$-maleimide, 3.51 ppm (s, PEG backbone), 4.58 ppm (t, —OH), 7.03 ppm (s, CH=CH maleimide).

Example 7

Diacid-free mPEG (20,000 Da)-propionic acid, N-hydroxysuccinimidyl ester

A mixture of methoxy-PEG (or M-PEG-OH) of molecular weight 20,000 Da containing 6 wt % of PEG-diol having molecular weight about 40,000 Da (HO-PEG-OH) (25.0 g), distilled water (25.0 ml) and potassium hydroxide (0.5 g) was cooled to 0-5° C. in an ice bath. Acetonitrile (3.4 g) was added slowly, and the solution was stirred for 2.5 hours at 0-5° C. The pH of the solution was adjusted to 7.0 by addition of phosphoric acid. The product was extracted with dichloromethane (200, 70, and 50 ml). The organic layer was dried over magnesium sulfate and added to cold ethyl ether. The precipitated product was removed by filtration and dried under vacuum giving 23.5 g of mPEG(20,000 Da) nitrile. NMR (d$_6$-DMSO): 2.74 ppm (t, —CH$_2$CN), 3.21 ppm (s, —OCH$_3$), 3.51 ppm (s, PEG backbone).

A mixture of mPEG nitrile from the above step (23.5 g) and concentrated hydrochloric acid (117.5 g) was stirred at room temperature for 36 hours. The solution was diluted with one liter of water and extracted with dichloromethane (200, 150, and 100 ml). The combined organic extracts were washed twice with water, dried over sodium sulfate, filtered, and concentrated to dryness by rotary evaporation. Yield of mPEG amide 21.5 g. NMR (d$_6$-DMSO): 2.26 ppm (t, —CH$_2$CONH$_2$), 3.21 ppm (s, —OCH$_3$), 3.51 ppm (s, PEG backbone).

mPEG amide from the above step (16.0 g) was dissolved in 1150 ml of distilled water, 100 g of potassium hydroxide was added, and the solution was stirred for 22 hours at room temperature. Sodium chloride (150 g) was added, and the solution was extracted with dichloromethane. The combined organic extracts were washed with 5% phosphoric acid, water (twice), and dried over sodium sulfate. The solution was concentrated and the product precipitated by addition to ethyl ether. The product, largely mPEG(20,000 Da) propionic acid, was collected by filtration and dried over vacuum. Yield of acid 14.0 g. NMR (d$_6$-DMSO): 2.43 ppm (t, —CH$_2$COOH), 3.21 ppm (s, —OCH$_3$), 3.51 ppm (s, PEG backbone).

Anion exchange chromatography showed that the product contained: PEG(40,000 Da)-dipropionic acid (6%), mPEG (20,000 Da)-propionic acid (91%), and mPEG(20,000 Da) (3%).

The above mixture was dissolved in distilled water (2,000 ml) and the resulting solution was filtered through the first chromatographic column (pre-column) filled with 50 ml of anion exchange gel: DEAE SEPHAROSE® Fast Flow (Pharmacia).

Anion exchange chromatographic analysis showed that the filtrate contained only mPEG(20,000 Da)-propionic acid and PEG(20,000 Da). All of the PEG(40,000 Da)-dipropionic acid and part of the m-PEG(20,000 Da)-propionic acid were adsorbed (retained) by the gel.

Next, the solution was applied on the second column (main column) containing 600 ml of DEAE SEPHAROSE® Fast Flow gel. Anion exchange chromatography showed that the eluate from the column contained only PEG(20,000 Da). mPEG(20,000 Da)-propionic acid, adsorbed on the column, was eluted using 5% NaCl solution (1100 ml). The pH of the eluate was adjusted to 7 and the product was extracted with dichloromethane. The extract was dried with anhydrous magnesium sulfate and added to ethyl ether. The precipitated product was filtered off and dried under reduced pressure. Yield 12.0 g. NMR (d$_6$-DMSO): 2.43 ppm (t, —CH$_2$COOH), 3.21 ppm (s, —OCH$_3$), 3.51 ppm (s, PEG backbone).

Anion exchange chromatography: mPEG(20,000 Da)-propionic acid 100%. No PEG(40,000 Da)-dipropionic acid was detected.

Diacid-free mPEG (20,000 Da) propionic acid (4.0 g, 0.20 mmol) was dissolved in dichloromethane (20 ml) and N-hydroxysuccinimide (0.21 mmol) was added. The solution was cooled to 0° C., a solution of dicyclohexylcarbodiimide (0.20 mmol) in 4 ml dichloromethane was added dropwise, and the solution was stirred at room temperature overnight. The reaction mixture was filtered, concentrated, and precipitated by addition to ethyl ether. Yield of final product: 3.8 g. NMR (d$_6$-DMSO): 2.81 ppm (s, NHS), 2.92 ppm (t, —CH$_2$—COO—), 3.21 ppm (s, —OCH$_3$), 3.51 ppm (s, PEG backbone).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

It is claimed:

1. A method for forming a functionalized polymer, comprising:
   (a) functionalizing HO-POLY-OH polymers in a substantially pure composition of HO-POLY-OH polymers to effect the introduction of one or more of the same functional group, Y, onto HO-POLY-OH under conditions effective to form from 8 to 45 percent of monosubstituted polymers of the formula HO-POLY-L-Y, no more than 40 percent of disubstituted polymers of the formula Y-L-POLY-L-Y, and about 65 to 91 percent of the unsubstituted HO-POLY-OH, and wherein no other functional group other than the functional group Y functionalizes the HO-POLY-OH polymers; and
   (b) purifying to provide a composition comprising monosubstituted polymers of the formula HO-POLY-L-Y substantially free from the unsubstituted polymers of the formula HO-POLY-OH and disubstituted polymers of the formula Y-L-POLY-L-Y,
   wherein POLY is a water-soluble and non-peptidic polymer, Y is a functional group in protected or unprotected form, and L is a linking group.

2. The method of claim 1, wherein said water-soluble and non-peptidic polymer is selected from the group consisting of poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(vinyl alcohol), polyphosphazene, polyoxazoline, poly(N-acryloylmorpholine), and copolymers, terpolymers, and mixtures thereof.

3. The method of claim 1, wherein said water-soluble and non-peptidic polymer is poly(ethylene glycol).

4. The method of claim 1, wherein the water-soluble and non-peptidic polymer provided in (a) is in a solvent selected from the group consisting of an organic solvent, water, a mixture of water and a water miscible solvent, and a mixture of water and an immiscible organic solvent.

5. The method of claim 4, wherein said organic solvent is selected from the group consisting of aromatic hydrocarbons, chlorinated hydrocarbons, amides, esters, ethers, ketones, and organonitriles.

6. The method of claim 4, wherein said organic solvent is selected from the group consisting of toluene, xylenes, benzene, dichloromethane, chloroform, acetonitrile, dimethoxyethane, tetrahydrofuran, dioxane, dimethylformamide, acetone, and mixtures thereof.

7. The method of claim 1, wherein the molecular weight of the polymer from about 100 Da to about 100,000 Da.

8. The method of claim 1, wherein the molecular weight of the polymer is from about 500 Da to about 60,000 Da.

9. The method of claim 1, wherein the molecular weight of the polymer is from about 5,000 to about 40,000 Da.

10. The method of claim 1, wherein said functionalizing is carried out under conditions effective to form no more than about 12 percent of the disubstituted polymer.

11. The method of claim 1, wherein said functionalizing is carried out under conditions effective to form no more than about 8 percent of the disubstituted polymer.

12. The method of claim 1, wherein said functionalizing is carried out under conditions effective to form no more than about 5 percent of the disubstituted polymer.

13. The method of claim 1, wherein said functionalizing is carried out under conditions effective to form no more than about 2 percent of the disubstituted polymer.

14. The method of claim 1, wherein said functionalizing is carried out under conditions effective to form no more than about 1 percent of the disubstituted polymer.

15. The method of claim 1, wherein said functionalizing is conducted under conditions effective to form a ratio of monosubstituted polymer to disubstituted polymer that is about 2:1 to about 40:1.

16. The method of claim 1, wherein said functionalizing is conducted under conditions effective to form a ratio of monosubstituted polymer to disubstituted polymer that is about 4:1 to about 20:1.

17. The method of claim 1, wherein said functionalizing is conducted under conditions effective to form a ratio of monosubstituted polymer to disubstituted polymer that is about 10:1 to about 18:1.

18. The method of claim 1, wherein Y is a protected functional group, and step (b) further comprises, after said functionalizing, deprotecting said protected functional group.

19. The method of claim 18, wherein Y is a protected carboxylic acid and said deprotecting comprises hydrolyzing said protected carboxylic acid to thereby form a carboxylic acid.

20. The method of claim 19, wherein said protected carboxylic acid is selected from the group consisting of esters, thiolesters, amides, amidates, thioamidates and hydrazides.

21. The method of claim 19, wherein said protected carboxylic acid is an ortho ester.

22. The method of claim 21, wherein Y is a protected amine.

23. The method of claim 22, wherein Y is a carbonitrile or primary amide and said deprotecting step comprises reducing the carbonitrile or primary amide to thereby form an amine.

24. The method of claim 1, wherein said functionalizing comprises a nucleophilic substitution or a nucleophilic addition reaction.

25. The method of claim 1, wherein Y is selected from the group consisting of aldehyde hydrate, ketone hydrate, amine, hydrazide, thiol, carboxylic acid, primary amide, secondary amide, amidate, 2-substituted-1,3-oxazoline, 2-substituted 1,3-(4H)-dihydrooxazines, 2-substituted-1,3-thiazoline, 2-substituted 1,3-(4H)-dihydrothiazines, dithiopyridine, vinylpyridine, hydroxylamine, and oxime.

26. The method of claim 1, wherein said functionalizing is carried out with a compound of the structure X—(CR$_1$R$_2$)$_m$—Y, wherein X is a group that reacts with a hydroxyl, optionally in anionic form, or with a carbon atom to which the hydroxyl is attached, in a nucleophilic substitution or nucleophilic addition reaction, R$_1$ and R$_2$ are each independently either H or alkyl, and m ranges from 0 to 10.

27. The method of claim 15, wherein said functionalizing is carried out with a compound of the structure X—(CR$_1$R$_2$)$_m$—Y, wherein X is a group that reacts with a hydroxyl, optionally in anionic form, or with a carbon atom to which the hydroxyl is attached, in a nucleophilic substitution or nucleophilic addition reaction, R$_1$ and R$_2$ are each independently either H or alkyl, m ranges from 0 to 10, and Y has the structure —C(O)—O—R$_p$, wherein R$_p$ is an alkyl or a substituted alkyl group.

28. The method of claim 26, wherein X is selected from the group consisting of a leaving group, a substituted vinyl group, or an unsubstituted vinyl group.

29. The method of claim 28, wherein X is a halogen or a sulfonate ester.

30. The method of claim 1, comprising the step of alkylating the non-peptidic polymer comprising two hydroxyl groups prior to step (b), or alkylating the mixture formed in step (b) prior to or subsequent to the purification step (c).

31. The method of claim 30, wherein said alkylating step comprises treating the mixture with an alkylating agent selected from the group consisting of dialkylsulfate, alkyl sulfonate, diazoalkane, alkyl halide, N,N-dimethylformamide dialkyl acetal, 3-alkyl-1-p-tolyltriazene, trimethylanilinium hydroxide, trialkyloxonium fluoroborate, trimethylsulfonium hexafluorophosphonate, and alkyl trichloroacetimidate.

32. The method of claim 30, wherein said alkylating is effective to convert hydroxyl groups in said mixture to —OR', wherein R' is an organic radical having 1-20 carbon atoms.

33. The method of claim 32, wherein R' is selected from the group consisting of methyl, ethyl, propyl, butyl, pentyl, hexyl, and benzyl.

34. The method of claim 1, further comprising prior to step (b), converting a portion of said polymer hydroxyls to a leaving group, Y, to thereby form a first mixture comprising the water soluble and non-peptidic polymer from step (a), a monosubstituted polymer comprising a single Y group, and a disubstituted polymer comprising two Y groups, under conditions effective to form no more than about 45 percent of the disubstituted polymer.

35. The method of claim 1, wherein Y is an ionizable functional group and said purifying step comprises purifying the mixture by ion exchange chromatography.

36. The method of claim 35, wherein said purifying step comprises:
   passing the mixture formed in step (b) through a first ion exchange column to provide an eluate, wherein said passing the mixture step is carried out under conditions effective to adsorb substantially all of said disubstituted polymer onto the first column;
   passing the eluate through a second ion exchange column under conditions effective to adsorb substantially all of the monosubstituted polymer onto said second column;
   washing the second column with a water or a solution having low ionic strength to remove unsubstituted polymer; and
   passing a solution having high ionic strength through the second column to desorb the monosubstituted polymer.

37. The method of claim 36, wherein said conditions in said eluting step comprise a column sufficiently sized to adsorb substantially all of said disubstituted polymer.

38. The method of claim 36, wherein said conditions in said purification step comprise one or more main columns sufficiently sized to adsorb substantially all of said monosubstituted polymer.

39. The method of claim 36, wherein said second ion exchange column is connected in series to one or more additional ion exchange columns, and said washing step further comprises washing said second and one or more additional ion exchange columns and said passing the eluate step further comprises passing the solution having high ionic strength through said second and one or more additional columns.

40. The method of claim 35, wherein said purifying step comprises:
   passing the mixture formed in step (b) through a first ion exchange column to provide an eluate, wherein said passing the mixture step is carried out under conditions effective to adsorb substantially all of said disubstituted polymer onto the first column;
   passing said eluate through a second ion exchange column connected in series to one or more additional ion exchange columns under conditions effective to adsorb a fraction of the monosubstituted polymer onto said second column;
   washing the second column and one or more additional ion exchange columns with a solution having low ionic strength to remove unsubstituted polymer;
   and passing a solution having high ionic strength through the second and one or more additional ion exchange columns to desorb the monosubstituted polymer.

41. A method for forming an alkylated functionalized polymer, said method comprising:
   (a) providing a water-soluble and non-peptidic polymer comprising two hydroxyl groups;
   (b) alkylating the water-soluble and non-peptidic polymer to form a mixture comprising (i) unalkylated water-soluble and non-peptidic polymer from step (a), (ii) a monoalkylated polymer comprising a single alkoxy group, and (iii) a dialkylated polymer comprising two alkoxy groups, under conditions effective to form at least about 25 mol percent of the dialkylated polymer;
   (c) reacting the mixture from step (b), in one or more reaction steps, with one or more functionalizing reagents to effect the introduction of a functional group, Y, to form a mixture comprising (i) unalkylated polymer comprising two Y groups, a monoalkylated polymer comprising a single Y group, and a dialkylated polymer comprising no Y groups; and
   (d) purifying the mixture from step (c) to provide a monoalkylated polymer substantially free from the unalkylated and dialkylated polymer species.

42. The method of claim 41, wherein one of said one or more functionalizing reagents additionally comprises —X, a group that reacts with a hydroxyl, optionally in anionic form, or with a carbon atom to which the hydroxyl is attached.

43. The method of claim 41, wherein said alkylating step is conducted under conditions effective to form an amount of dialkylated polymer that is at least about 40 mol percent of the dialkylated polymer.

44. The method of claim 41, wherein said alkylating step is conducted under conditions effective to form an amount of dialkylated polymer that is at least about 65 mol percent of the dialkylated polymer.

45. The method of claim 41, wherein said alkylating step is conducted under conditions effective to form an amount of dialkylated polymer that is at least about 90 mol percent of the dialkylated polymer.

46. The method of claim 1, wherein said functionalizing is carried out under conditions effective to form from 8 to 30 percent of the monosubstituted polymer.

* * * * *